(12) United States Patent
Looger et al.

(10) Patent No.: US 9,945,844 B2
(45) Date of Patent: Apr. 17, 2018

(54) GENETICALLY ENCODED CALCIUM INDICATORS AND METHODS OF USE

(71) Applicant: Howard Hughes Medical Institute, Chevy Chase, MD (US)

(72) Inventors: Loren Looger, Sterling, VA (US); Karel Svoboda, Leesburg, VA (US); Douglas Kim, Reston, VA (US); Rex Kerr, Leesburg, VA (US)

(73) Assignee: Howard Hughes Medical Institute, Chevy Chase, MD (US)

( * ) Notice: Subject to any disclaimer, the term of this patent is extended or adjusted under 35 U.S.C. 154(b) by 0 days.

(21) Appl. No.: 15/342,295

(22) Filed: Nov. 3, 2016

(65) Prior Publication Data

US 2017/0292943 A1     Oct. 12, 2017

Related U.S. Application Data

(62) Division of application No. 14/800,814, filed on Jul. 16, 2015, now Pat. No. 9,488,642, which is a division of application No. 13/801,120, filed on Mar. 13, 2013, now Pat. No. 9,518,980.

(60) Provisional application No. 61/711,995, filed on Oct. 10, 2012.

(51) Int. Cl.
*C07K 14/47* (2006.01)
*G01N 33/50* (2006.01)
*C07K 14/00* (2006.01)

(52) U.S. Cl.
CPC ..... *G01N 33/5041* (2013.01); *C07K 14/4728* (2013.01); *C07K 14/00* (2013.01); *C07K 2319/60* (2013.01); *G01N 2333/4727* (2013.01); *G01N 2500/10* (2013.01)

(58) Field of Classification Search
None
See application file for complete search history.

(56) References Cited

U.S. PATENT DOCUMENTS

| 9,488,642 B2 | 11/2016 | Looger et al. |
| 9,518,980 B2 | 12/2016 | Looger et al. |
| 2010/0154068 A1* | 6/2010 | Yu ..................... A01K 67/0275 800/3 |
| 2012/0034691 A1 | 2/2012 | Looger et al. |

FOREIGN PATENT DOCUMENTS

WO    WO 2011056975 A4 *  12/2011    ......... C07K 14/4728

OTHER PUBLICATIONS

Tian et al., Imaging neural activity in worms, flies and mice with improved GCaMP calcium indicators, Dec. 2009, Nature Methods 6(12):875-881.*
International Search Report and Written Opinion in International Application No. PCT/US2013/064355, dated Jan. 24, 2014, 15 pages.
Airan et al., "Temporally precise in vivo control of intracellular signaling," *Nature*, 2009, 458(7241):1025-1029.
Akerboom et al., "Crystal Structures of the GCaMP Calcium Sensor Reveal the Mechanism of Fluorescence Signal Change and Aid Rational Design," *J. Biol. Chem.*, 2009, 284:6455-64.
Akerboom et al., "Optimization of a GCaMP Calcium Indicator for Neural Activity Imaging," *J. Neurosci.*, 2012, 32:13819-40.
Brenner et al., "An automated microscope for cytologic research a preliminary evaluation," *J. Histochem. Cytochem.*, 1976, 24:100-11.
Hsu and Luo, "Molecular dissection of G protein preference using Gsα chimeras reveals novel ligand signaling of GPCRs," *Am J Physiol Endocrinol Metab.*, 2007, 293(4):E1021-E1029.
Jones et al., "Voronoi-Based Segmentation of Cells on Image Manifolds," *Computer Vision for Biomedical Image Applications*, Springer-Verlag, 2005, 3765:535-543.
Kerr et al., "Imaging input and output of neocortical networks in vivo," *PNAS USA*, 2005, 102:14063-8.
Kralj et al., "Optical recording of action potentials in mammalian neurons using a microbial rhodopsin," *Nat. Methods*, 2012, 9:90-5.
NCBI, GenBank accession No. ADJ53338.1, Jul. 4, 2010, 2 pages.
NCBI, GenBank accession No. HM143847.1, Jul. 4, 2010, 2 pages.
VanScyoc et al., "Calcium Binding to Calmodulin Mutants Monitored by Domain-Specific Intrinsic Phenylalanine and Tyrosine Fluorescence," *Biophys. J.*, 2002, 83:2767-80.
Zhang et al., "Evaluation of FLIPR Calcium 3 Assay Kit—A New No-Wash Fluorescence Calcium Indicator Reagent," *J Biomol Screen*, 2003, 8(5):571-577.

* cited by examiner

*Primary Examiner* — John D Ulm
(74) *Attorney, Agent, or Firm* — Fish & Richardson P.C.

(57) ABSTRACT

Genetically encoded calcium indicator (GECI) polypeptides and the nucleic acid molecules encoding such polypeptides are provided. In addition, methods of using such nucleic acids and polypeptides in methods of screening for agonists or antagonists of G-protein coupled receptor (GPCR) or ion channels and methods of monitoring neural activity also are provided.

9 Claims, 26 Drawing Sheets

FIG 1A
FIG 1D
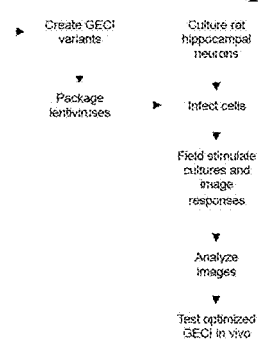
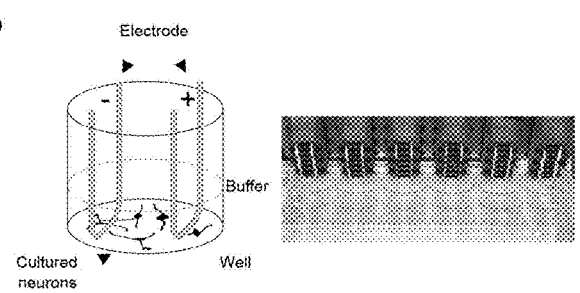
FIG 1B
FIG 1C
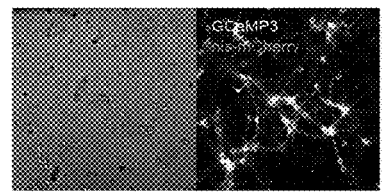
FIG 1E
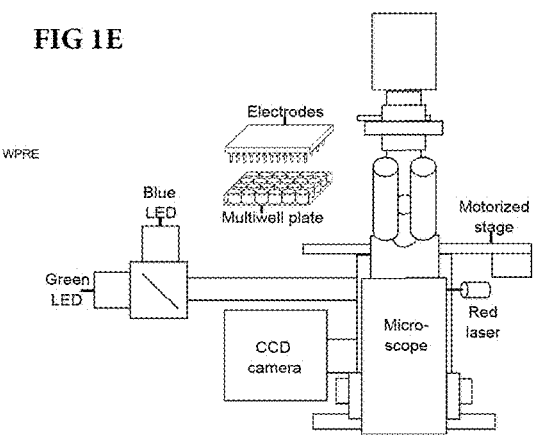

FIG 2A
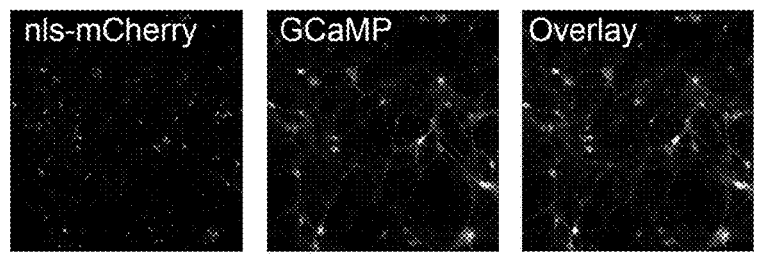
↓
nls-mCherry channel    FIG 2B
↓
Low pass filtering    →    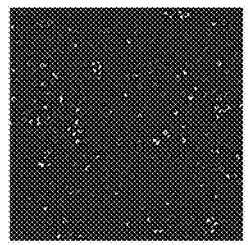  Filtered mCherry
↓
Finding local maxima    FIG 2C
↓
Adaptive thresholding    →    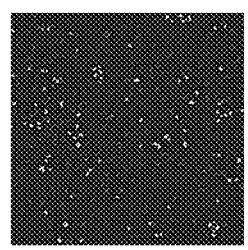  Local maxima + Voronoi diagram
↓
Voronoi diagram
FIG 2D
↓
Local adaptive thresholding GCaMP/mCherry channel    →    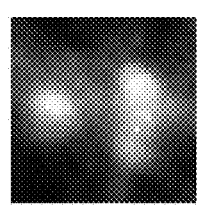   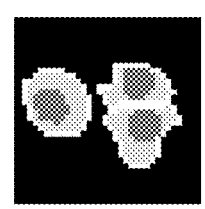
↓    FIG 2E
Quality control and Final segmentation    →       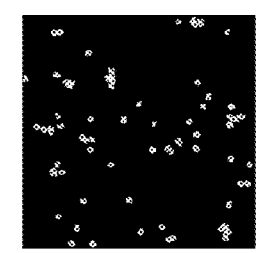

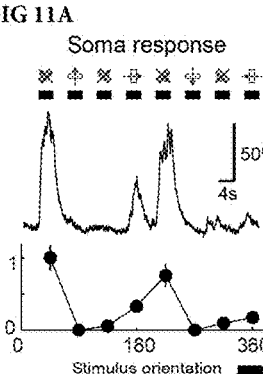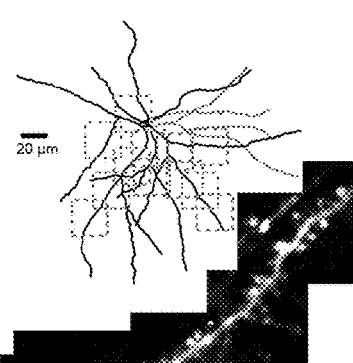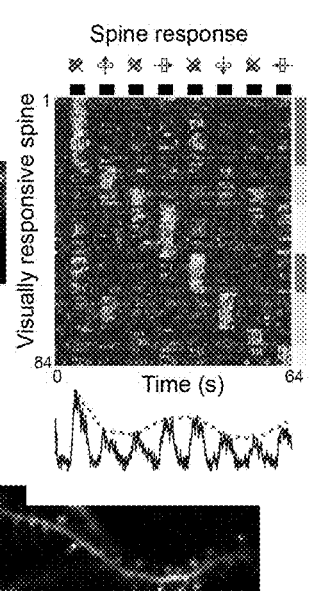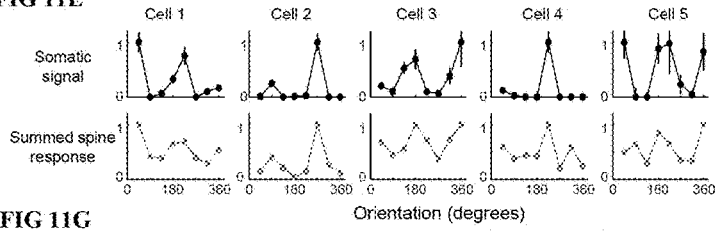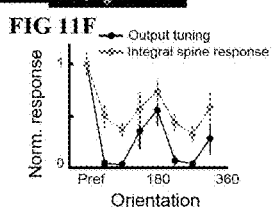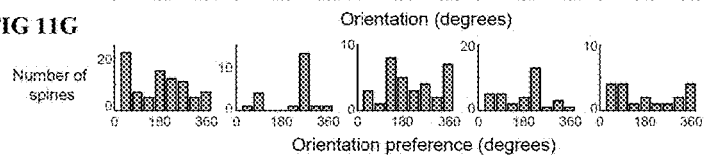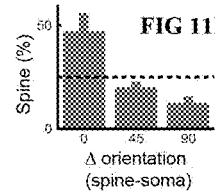

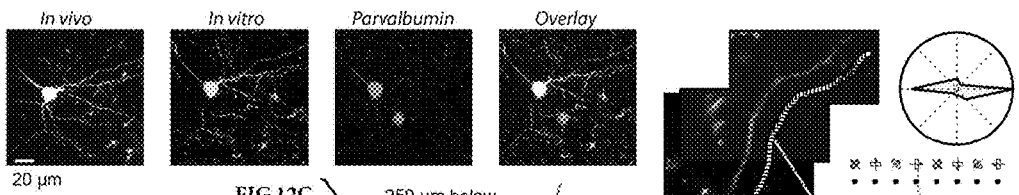
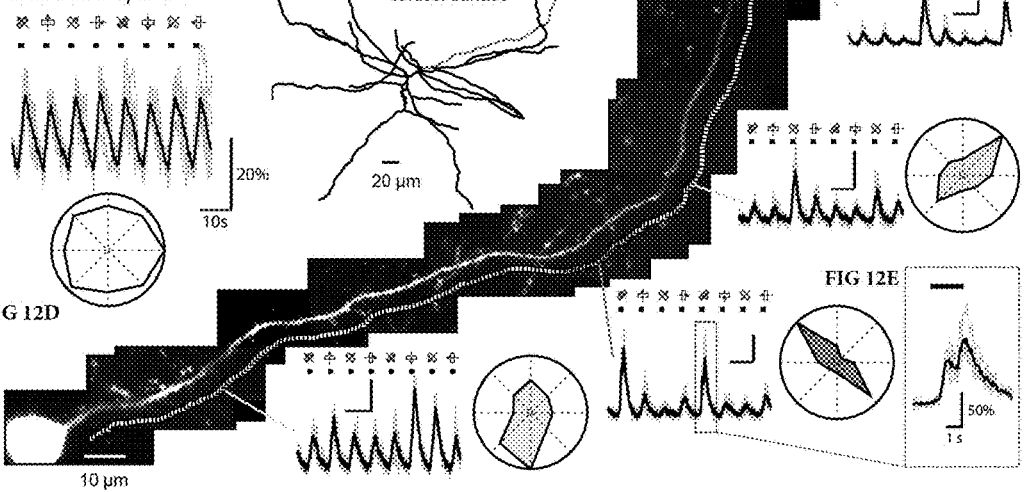
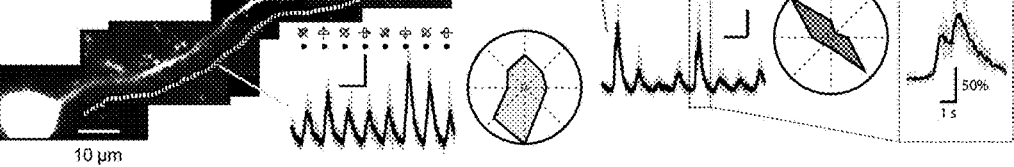
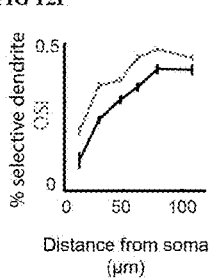
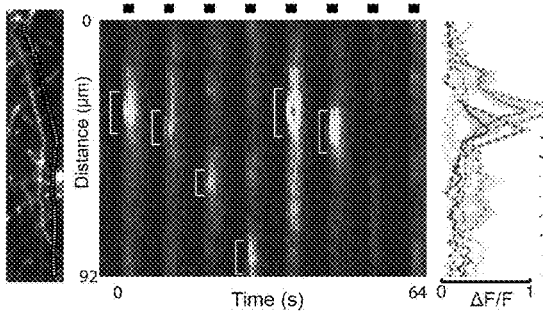
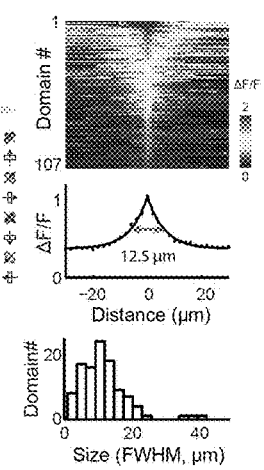

FIG 14A
FIG 14B
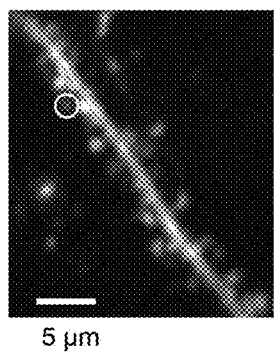
5 μm
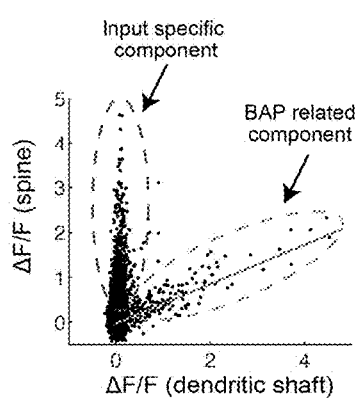
Input specific component
BAP related component
ΔF/F (spine)
ΔF/F (dendritic shaft)
FIG 14C    FIG 14D    FIG 14E    FIG 14F    FIG 14G
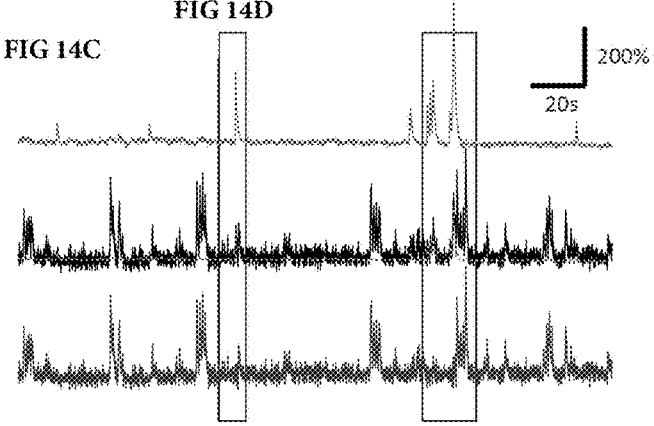
······· dF/F (dendritic shaft)
─── dF/F (spine)
······· predicted BAP componet
═══ BAP removed spine signal Number of action potentials in 250ms bin

OSI

GENETICALLY ENCODED CALCIUM INDICATORS AND METHODS OF USE

CROSS REFERENCE TO RELATED APPLICATIONS

This application is a divisional of U.S. patent application Ser. No. 14/800,814 filed Jul. 16, 2015, which is a divisional of U.S. patent application Ser. No. 13/801,120 filed Mar. 13, 2013, which claims priority under 35 USC § 119(e) to U.S. Application No. 61/711,995 filed Oct. 10, 2012.

BACKGROUND

Calcium is a universal second messenger regulating essential cellular signaling events in a broad range of cells, tissues and organisms. In neurons, action potentials (APs) trigger large and rapid changes in cytoplasmic free calcium. Similarly, activation of synaptic glutamate receptors during synaptic transmission produces $Ca^{2+}$ in dendritic spines. Calcium imaging using synthetic calcium indicators has been used to measure neuronal spiking and synaptic input across populations of neurons in vitro and in vivo. However, synthetic indicators are difficult to target to specific cell types or sub-cellular locations, and the loading procedures are invasive and damaging to neural tissue, precluding repeated, chronic in vivo measurements.

SUMMARY

In one aspect, a nucleic acid molecule encoding a genetically encoded calcium indicator (GECI) polypeptide is provided, wherein the GECI polypeptide comprises an amino acid sequence having at least 95% sequence identity to a sequence shown in SEQ ID NO:2, SEQ ID NO:4, SEQ ID NO:6, SEQ ID NO:8 or SEQ ID NO:10. In some embodiments, the GECI comprises an amino acid sequence having at least 99% sequence identity to a sequence shown in SEQ ID NO:2, SEQ ID NO:4, SEQ ID NO:6, SEQ ID NO:8 or SEQ ID NO:10. In some embodiments, the GECI comprises an amino acid sequence shown in SEQ ID NO:2, SEQ ID NO:4, SEQ ID NO:6, SEQ ID NO:8 or SEQ ID NO:10. In some embodiments, the nucleic acid has the sequence shown in SEQ ID NO:1, SEQ ID NO:3, SEQ ID NO:5, SEQ ID NO:7 or SEQ ID NO:9. Also provided is a vector comprising any of the above-described nucleic acid molecules. Also provided is a cell comprising such a vector, or a cell comprising any of the above-described nucleic acid molecule.

In another aspect, a GECI polypeptide is provided, wherein the polypeptide comprises an amino acid sequence having at least 95% sequence identity to a sequence shown in SEQ ID NO:2, SEQ ID NO:4, SEQ ID NO:6, SEQ ID NO:8 or SEQ ID NO:10. In some embodiments, the polypeptide comprises an amino acid sequence having at least 99% sequence identity to a sequence shown in SEQ ID NO:2, SEQ ID NO:4, SEQ ID NO:6, SEQ ID NO:8 or SEQ ID NO:10. In some embodiments, the polypeptide comprises an amino acid sequence shown in SEQ ID NO:2, SEQ ID NO:4, SEQ ID NO:6, SEQ ID NO:8 or SEQ ID NO:10. Also provided is a cell comprising any of the above-described polypeptides. In some embodiments, such a cell further comprises a nucleic acid molecule encoding a G-protein coupled receptor (GPCR) polypeptide. In some embodiments, such a cell further comprises a nucleic acid molecule encoding an ion channel. In some embodiments, the nucleic acid molecule encoding the GPCR polypeptide or the ion channel is heterologous to the cell.

In still another aspect, a method of screening agents for agonists or antagonists of G-protein coupled receptor (GPCR) polypeptides is provided. Generally, such a method includes (i) contacting a test agent with a cell comprising a GPCR polypeptide and a genetically encoded calcium indicator (GECI) polypeptide, wherein the GECI polypeptide comprises an amino acid sequence having at least 95% sequence identity to SEQ ID NO:2, SEQ ID NO:4, SEQ ID NO:6, SEQ ID NO:8 or SEQ ID NO:10; and (ii) determining a level of fluorescence produced by the cell. Typically, an increase in fluorescence relative to a control indicates that the test agent is an agonist of the GPCR polypeptide, and a decrease in fluorescence relative to a control indicates that the test agent is an antagonist of the GPCR polypeptide. In some embodiments, the cell is in vitro. In some embodiments, the cell is in vivo (e.g., in a mouse, a worm, a rat, or a fly).

In some embodiments, the agent is selected from the group consisting of a nucleic acid, a polypeptide, a small molecule and combinations thereof. In some embodiments, the nucleic acid is an inhibitory nucleic acid. Representative inhibitory nucleic acids include, without limitation, a triplex forming oligonucleotide, an aptamer, a ribozyme, an antisense RNA, a short interfering RNA (siRNA), or a micro-RNA (miRNA). In some embodiments, the polypeptide is an antibody.

In still another aspect, a method of monitoring the activity of a cell is provided. Generally, such a method includes (i) providing a cell comprising a GPCR and a GECI, wherein the GECI comprises an amino acid sequence having at least 95% sequence identity to a sequence shown in SEQ ID NO:2, SEQ ID NO:4, SEQ ID NO:6, SEQ ID NO:8 or SEQ ID NO:10; (ii) stimulating the cell; and (iii) detecting the fluorescence emitted by the cell. In some embodiments, the cell is provided in a biological sample from a subject (e.g., a mouse, a worm or a fly). In some embodiments, the detecting step comprises imaging. In some embodiments, the cell is a neuronal cell, a muscle cell or a cardiomyocyte.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

BRIEF DESCRIPTION OF THE DRAWINGS

FIG. 1A is a schematic of a pipeline for GECI optimization on screening the platform. FIG. 1B is a schematic of the prolentiviral vector containing the human synapsin-1 promoter (syn), GCaMP variant, internal ribosome entry site (IRES), nuclear localization signal fused with mCherry (nls-mCherry), and woodchuck hepatitis post-transcriptionalregulatory element (WPRE). FIG. 1C is an epifluorescence image showing GCaMP3-positive cells (green) and nls-mCherry-positive nuclei (red). Scale bar: 100 μm. FIG. 1D is a schematic of electrodes immersed in buffer above the cultured neurons. The photo shows a 24-well cap stimulator with pairs of parallel platinum wires. FIG. 1E is a schematic of the screening platform.

FIG. 2A shows epifluorescence images of the nls-mCherry fluorescence channel, GCaMP fluorescence channel, and overlayed channels. FIG. 2B is the nls-mCherry fluorescence channel after low-pass frequency filtering with a circular kernel to identify putative nuclei. FIG. 2C is a filtered image where local intensity maxima were identified using adaptively defined thresholds followed by cutting of the image into a Voronoi diagram based on seeds identified by maxima. FIG. 2D shows images from inset in (a, overlay) before and after adaptive thresholding in the GCaMP and mCherry channels within each sub-region to define pixels that belong to cytosol and nuclei. FIG. 2E shows images before and after final segmentation, where ROIs were excluded if the average mCherry level did not reach a predefined threshold and if the ROIs touched the image boundary.

FIG. 9A-bottom shows color-coded representative fields of view from experiments using GCaMP5G (left) and GCaMP6s (right). Moving gratings are shown to the mouse in the 4 cardinal directions, and orientation selectivity is computed using standard methods. The resulting orientation sensitivity is shown in the 4 cardinal directions (red, cyan, green, yellow) by color intensity. GCaMP6s annotates much more of a representative field of view as orientation-selective than GCaMP5G does, revealing its larger response to action potentials.

FIG. 10I-right shows the fluorescence responses of the same spine to eight oriented gratings recorded over days. The orientation-selective properties of the single spine are stable over weeks. FIG. 10K-bottom shows the distribution of ΔOri (difference in orientation tuning between two sessions) of the visually responsive spines. Most, but not all, spines remain tuned to the same orientation selectivity over the course of the week. Some spines modulate their orientation selectivity by up to ~75 degrees.

FIG. 11A shows the somatic fluorescence responses of a GCaMP6s-expressing layer 2/3 pyramidal neuron to oriented drifting gratings (top) and the corresponding tuning curve (bottom, normalized). FIG. 11B shows reconstruction of the dendritic arbor based on GCaMP6s fluorescence. FIG. 11C shows the fluorescence responses (ΔF/F) of visually responsive spines (69/298) sorted by their preferred orientation averaged over 5 trials. Top: each row shows one spine normalized to its peak; Bottom: summed ΔF/F across all spines. FIG. 11D shows the locations of orientation selective spines on a subset of imaged dendrites (corresponding to red dendrites in FIG. 11B). FIG. 11E shows the tuning curve of somatic ΔF/F (top) and the summed spine ΔF/F (bottom). FIG. 11F shows the averaged output tuning (black) and integral spine response (gray) across the 5 sampled neurons. The turning curves were aligned to the preferred orientation of the output response (0 degree). FIG. 11G shows the distribution of preferred orientation of dendritic spines (5 cells; number of spines sampled: 298,166,137,278,116). FIG. 11H shows the fraction of visually responsive spines preferring orientations 0, 45 or 90 degree away from the postsynaptic cell's preferred orientation.

FIG. 12A shows a GCaMP6s-expressing interneuron, identified posthoc as a parvalbumin-positive interneuron. FIG. 12B shows that somatic fluorescence changes to oriented drifting grating (same cell as in FIG. 12A). FIG. 12C shows reconstruction of the dendritic arbor based on GCaMP6s fluorescence. FIG. 12D on the left shows a dendrite of the cell (red in FIG. 12C) was imaged along its entire length. Colored squares indicate dendritic sites showing significant orientation tuning (p<0.01, ANOVA across 8 stimulus directions). The color of each square indicates the local preferred orientation, and the saturation of the color encodes the orientation selectivity index (OSI=1, saturated color; OSI=0, white). FIG. 12D on the right shows an example dendritic fluorescence changes and the corresponding polar plots for four locations with distinct orientation preference. FIG. 12E shows that the dendritic calcium signal shows modulation at the frequency of the drifting grating (1 Hz). FIG. 12F shows the OSI and fraction of orientation-selective dendritic sites plotted against the distance from soma (3425 sites, 5 cells). FIG. 12G on the left shows a dendritic segment labeled with GCaMP6. Orientation-selective sites are indicated by colored squares. FIG. 12G in the middle show color-coded fluorescence responses of 92 dendritic ROIs (1 micrometer spacing) averaged over 5 trials. Each row shows the response of one ROI. White brackets indicate dendritic domains with peak ΔF/F>40%. FIG. 12G on the right shows the peak ΔF/F averaged over two second stimulus periods plotted against distance. Each stimulus orientation was plotted using a different color. FIG. 12H shows the spatial profiles for 107 dendritic domains aligned to the location of the peak response (top and middle) and averaged ΔF/F across all domains (bottom).

FIG. 14A shows a segment of pyramidal cell dendrite labeled with GCaMP6s. A region covering the parent dendritic shaft (red) was drawn to measure global, BAP related dendritic signal. Spine signals were measured from circular regions covering individual spines (yellow). FIG. 14B shows that the contribution of the global dendritic signal to the spine signal was estimated using robust regression. FIG. 14C shows an example dendritic shaft signal (red), spine signal (black), the predicted BAP component of the spine signal (dash red line; i.e., shaft signal scaled by the slope of the fitted line in FIG. 14B), and BAP removed, input specific spine signal (blue). FIG. 14F and FIG. 14G show an enlarged view or the boxed regions in FIG. 14D and FIG. 14E, respectively.

DETAILED DESCRIPTION

Figure 3A:
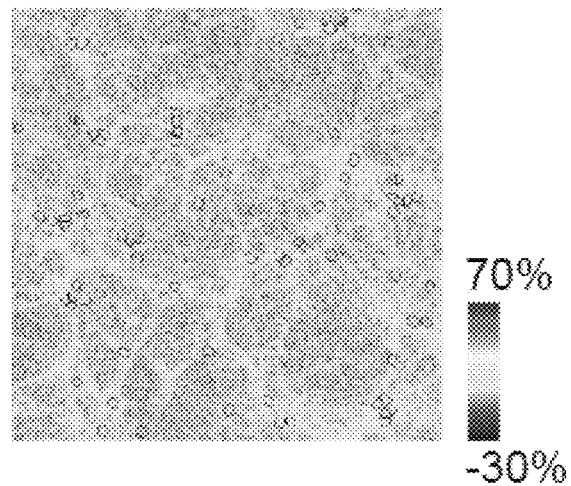
FIG. 3A shows the 3AP ΔF/F0 response map for GCaMP3 (red: high response, blue: low response, black outlines: ROI)

Genetically encoded calcium indicators (GECIs) (also called fluorescent calcium indicator proteins; FCIPs) provide an alternative to synthetic indicators. GECIs can be easily targeted to specific cell types or sub-cellular compartments, and are compatible with long-term, repeated in vivo measurements. GECIs consist of a calcium-binding domain such as calmodulin or troponin C, fused to one or more (e.g., one, two, three, four, or more) fluorescent proteins (FPs). In single-FP GECIs, the fluorescence intensity of a circularly permuted FP (cpFP) is modulated by calcium binding-dependent changes in the chromophore environment. In two-FP GECIs and multiple-FP GECIs, calcium binding modulates fluorescence resonance energy transfer (FRET) between FPs.

The calmodulin-based FRET indicator D3cpVenus (D3cpV) has recently been reported to detect single action potentials (APs) in pyramidal neurons in organotypic mouse brain slices and in vivo. The troponin C-based indicator TN-XXL has been used for chronic in vivo activity imaging in the mouse brain. Among single-FP based GECIs, the GCaMP family has found the broadest use across multiple model organisms. However, the properties of all available GECIs are still inferior to synthetic indicators in terms of signal-to-noise ratio (SNR), response linearity, photostability, and properly tuned calcium affinity. The GCaMP indicators further suffer from poor protein stability.

Nucleic Acid and Polypeptide Compositions

As described herein, improved GCaMP variants ("GCaMP5" and "GCaMP6") were developed and characterized. As shown in the examples below, the GCaMP variants described herein show dramatically improved responses in neurons to action potential (AP) stimulation, particularly for small numbers of APs. Thus, the variants disclosed herein are more sensitive at detecting neural activity than previous variants. Further, the variants disclosed herein show significantly faster rise and decay kinetics to AP-evoked calcium transients. Thus, the variants disclosed herein are better able to resolve and quantitate trains of APs and to precisely measure the times of APs. The variants disclosed herein also can differentiate between lower-frequency spike-firing rates and higher-frequency spike-firing rates. The variants disclosed herein also are brighter in their calcium-bound, activated state than previous variants.

Provided herein are nucleic acid sequences encoding genetically encoded calcium indicators (GECIs) such as those designated GCaMP5G GCaMP5K, GCaMP6s, GCaMP6m, and GCaMP6f. In some embodiments, the encoded GCaMP5 or GCaMP6 polypeptide comprises the amino acid sequence shown in SEQ ID NO: 2, SEQ ID NO:4, SEQ ID NO:6, SEQ ID NO:8 or SEQ ID NO:10, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:4, SEQ ID NO:6, SEQ ID NO:8 or SEQ ID NO:10 is expressed as a percentage of the total number of amino acids present. For example, about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, 30%, 40%, 50%, or a range between any two of the aforementioned numbers, of the amino acids present in SEQ ID NO: 2, SEQ ID NO:4, SEQ ID NO:6, SEQ ID NO:8 or SEQ ID NO:10 can be substituted with a conservative amino acid(s), so long as the desired function of the peptide is maintained (e.g., substantially maintained). For example, in some instances, the nucleic acid sequence can comprise SEQ ID NO:1, SEQ ID NO:3, SEQ ID NO:5, SEQ ID NO:7 or SEQ ID NO:9. In some embodiments, the nucleic acid sequence can consist or consist essentially of SEQ ID NO:1, SEQ ID NO:3, SEQ ID NO:5, SEQ ID NO:7 or SEQ ID NO:9.

Also provided are GCaMP5 and GCaMP6 polypeptides. For example, a GCaMP5 or GCaMP6 polypeptide can have a sequence that comprises SEQ ID NO: 2, SEQ ID NO:4, SEQ ID NO:6, SEQ ID NO:8 or SEQ ID NO:10, optionally with one or more conservative amino acid substitutions (e.g., with one, two, three, four, five, six, seven, eight, nine, ten, fifteen, twenty, or a range between any two of the aforementioned numbers, or more than twenty conservative amino acid substitutions, so long as the desired function of the peptide is maintained (e.g., substantially maintained). In some embodiments, the number of amino acid substitutions in SEQ ID NO: 2, SEQ ID NO:4, SEQ ID NO:6, SEQ ID NO:8 or SEQ ID NO:10 is expressed as a percentage of the total number of amino acids present. For example, about 0.5%, 1.0%, 1.5%, 2.0%, 2.5%, 3.0%, 3.5%, 4.0%, 4.5%, 5.0%, 5.5%, 6.0%, 6.5%, 7%, 7.5%, 8.0%, 8.5%, 9.0%, 9.5%, 10.0%, 15%, 20%, 25%, or 30% (or a range between any of the aforementioned numbers) of the amino acids present in SEQ ID NO:2, SEQ ID NO:4, SEQ ID NO:6, SEQ ID NO:8 or SEQ ID NO:10 can be substituted with a conservative amino acid(s), so long as the desired function of the peptide is maintained (e.g., substantially maintained)). In addition to a substitution, an insertion or a deletion can be introduced into a GCaMP5 or GCaMP6 polypeptide. Insertions include the introduction of single or multiple amino acid residues, while deletions are characterized by the removal of one or more amino acid residues. Methods for predicting tolerance to protein modification are known in the art (see, e.g., Guo et al., 2004, PNAS USA, 101(25):9205-9210).

Nucleic acids that encode the polypeptide sequences, variants, and fragments thereof are disclosed. These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every nucleic acid sequence is in fact disclosed and described herein through the disclosed polypeptide sequences.

A GECI polypeptide provided herein, or a nucleic acid encoding such a GECI polypeptide, also provided herein, can have at least 70% sequence identity (e.g., at least 71%, 72%, 73%, or 74% sequence identity), at least 75% sequence identity (e.g., at least 76%, 77%, 78%, or 79% sequence identity), at least 80% sequence identity (e.g., at least 81%, 82%, 83%, or 84% sequence identity), at least 85% sequence identity (e.g., at least 86%, 87%, 88%, or 89% sequence identity), at least 90% sequence identity (e.g., at least 91%, 92%, 93%, or 94% sequence identity), at least 95% sequence identity (e.g., at least 96%, 97%, 98%, or 99% sequence identity) to a GECI polypeptide disclosed herein (e.g., SEQ ID NO:2, SEQ ID NO:4, SEQ ID NO:6, SEQ ID NO:8 or SEQ ID NO:10) or a nucleic acid disclosed herein that encodes for a GECI polypeptide (e.g., SEQ ID NO:1, SEQ ID NO:3, SEQ ID NO:5, SEQ ID NO:7 or SEQ ID NO:9).

A nucleic acid or polypeptide sequence can be compared to another sequence and described in terms of its percent sequence identity. In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer.

The alignment of two or more sequences to determine percent sequence identity is performed using the algorithm described by Altschul et al. (1997, Nucleic Acids Res., 25:3389-3402) as incorporated into BLAST (basic local alignment search tool) programs, available at ncbi.nlm.nih.gov on the World Wide Web. BLAST searches can be performed to determine percent sequence identity between a first nucleic acid and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence disclosed herein (e.g., SEQ ID NOs:1-10) and another sequence, the default parameters of the respective programs are used.

TABLE 1

Conservative Amino Acid Substitutions

| Amino Acid | Representative Conservative Amino Acids |
|---|---|
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |
| Thr | Ser, Val, Ala |
| Trp | Tyr, Phe |
| Tyr | Trp, Phe, His |
| Val | Ile, Leu, Met, Ala, Thr |

Modifications, including substitutions, insertions or deletions are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As described above, the GCaMP5 and GCaMP6 variants provided herein have the same or better characteristics than GCaMP3 (see, for example, WO 2011/056975 and Tian et al., 2009, Nat. Methods, 6(12):875-81). For example, the GCaMP5 and GCaMP6 variants have one or more of the following characteristics: the same or better affinity for calcium than GCaMP3, the same or better protein stability as GCaMP3, the same or better photostability as GCaMP3, the same or higher cooperativity (Hill coefficient) as GCaMP3, the same or better brightness as GCaMP3, the same or better sensitivity as GCaMP3, and/or the same or better kinetics as GCaMP3. The GCaMP5 and GCaMP6 variants can be compared to GCaMP3 using the methods described herein.

Also provided are vectors that include the GECI-encoding nucleic acid sequences disclosed herein. Typically, the GECI-encoding nucleic acid sequences comprise SEQ ID NO:1, SEQ ID NO:3, SEQ ID NO:5, SEQ ID NO:7 or SEQ ID NO:9, and sequences with identity thereto, as noted above. Similarly, the GECI polypeptide typically comprises SEQ ID NO: 2, SEQ ID NO:4, SEQ ID NO:6, SEQ ID NO:8 or SEQ ID NO:10, and sequences with identity thereto, as noted above. Examples of suitable vectors include, but are not limited to, plasmids, artificial chromosomes such as BACs, YACs, or PACs, and any of a number of viral vectors (e.g., retroviral vectors, replication-defective adenoviruses).

Vectors typically contain an origin of replication and one or more regulatory regions. Regulatory regions include, without limitation, promoters, enhancers, inducible elements, protein binding sequences, 5' or 3' untranslated regions (UTRs), transcriptional start sites, termination sequences, and poly-adenylation sequences.

Promoters may be obtained from various sources including, for example, viruses such as polyoma, Simian Virus 40 (SV40), adenovirus, retroviruses, hepatitis B virus, and cytomegalovirus (CMV), or promoters from mammalian cells, e.g. beta-actin promoter or EF1-alpha promoter. In addition, promoters native to the host cell also are useful herein.

Enhancers refer generally to nucleic acid sequences that affect transcription of a sequence. Enhances typically are able to act at a distance from the transcribed sequence, be 5' or 3' to, or within an intron of, the transcribed sequence, and/or can be in cis orientation to the transcribed sequence. Many enhancer sequences are known from mammalian genes (globin, elastase, albumin, fetoprotein, and insulin), as well as from viruses (e.g., the SV40 enhancer on the late side of the replication origin, the cytomegalovirus early promoter enhancer, the polyoma enhancer on the late side of the replication origin, and adenovirus enhancers).

A promoter and/or an enhancer can be inducible (e.g. chemically or physically regulated). A chemically-induced promoter and/or enhancer can be regulated by the presence of, for example, alcohol, tetracycline, a steroid, or a metal. A physically-induced promoter and/or enhancer can be regulated by, for example, environmental factors such as temperature or light. On the other hand, a promoter and/or enhancer can be constitutive. In addition, certain promoters and/or enhancers can be active in a cell type-specific manner.

Vectors also can include a selectable marker. A selectable marker typically confers a phenotype on a cell and allows the cell to survive when placed under selective pressure. The product of the selectable marker can be used to confirm that the vector has been delivered to the cell and is being expressed. Examples of selectable markers include, without limitation, dihydrofolate reductase (DHFR), thymidine kinase, neomycin, neomycin analog G418, hygromycin, puromycin, blasticidin, beta-galactosidase, beta-glucuronidase, green fluorescent protein (GFP), and luciferase.

In addition, a vector can include a sequence encoding a tag, which is designed to facilitate manipulation or detection (e.g., purification or localization) of the expressed polypeptide. Sequences encoding tags such as GFP, glutathione S-transferase (GST), polyhistidine, c-myc, hemagglutinin, or FLAG™ tag (Kodak; New Haven, Conn.) typically are expressed as a fusion with the encoded polypeptide (e.g., at either the carboxyl or amino terminus or within the polypeptide).

Cells comprising the GECIs, the GECI-encoding nucleic acid sequences or vectors comprising the GECI-encoding nucleic acid sequence are provided. The cell can be, for example, a eukaryotic or prokaryotic cell. Suitable cells include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), and insect cells (for example, Sf9). Suitable cells also include, but are not limited to, human cells and plant cells. Representative human cells include, for example, HeLa cells or human embryonic kidney (HEK) cells. Cells that can be used herein are commercially available from, for example, the American Type Culture Collection (ATCC; PO Box 1549, Manassas, Va. 20108). See also Ausubel et al., 1998, Current Protocols in Molecular Biology, John Wiley & Sons, New York, N.Y. In some instances, the GECI-encoding nucleic acid sequence can be located in the genome of the cell. In some embodiments, the cell also includes a nucleic acid encoding a G-protein coupled receptor (GPCR) or an ion channel. Such a nucleic acid encoding a GPCR or an ion channel can be heterologous or endogenous to the cell.

Methods of introducing nucleic acids into cells are known and the method of transformation and choice of expression vector will depend on the host system selected. Transformation and transfection methods are described, e.g., in Ausubel et al. (1998, Current Protocols in Molecular Biology, John Wiley & Sons, New York, N.Y., (1998)), and, as described above, expression vectors may be chosen from examples known in the art. There are a number of compositions and methods which can be used to deliver the nucleic acid molecules and subsequently encoded polypeptides to cells, either in vitro or in vivo via. These methods and compositions can largely be broken down into two classes: viral-based delivery systems and non-viral-based delivery systems. Such delivery systems are well known in the art and are readily adaptable for use with the compositions and methods described herein.

Simply by way of example, polypeptides and/or nucleic acid molecules can be delivered via virus-like particles. Virus-like particles (VLPs) consist of viral protein(s) derived from the structural proteins of a virus. Methods for making and using virus-like particles are described in, for example, Garcea and Gissmann (2004, Current Opinion in Biotechnology, 15:513-7). Polypeptides also can be delivered by subviral dense bodies (DBs). DBs transport proteins into target cells by membrane fusion. Methods for making and using DBs are described in, for example, Pepperl-Klindworth et al. (2003, Gene Therapy, 10:278-84). In addition, polypeptides can be delivered by tegument aggregates. Methods for making and using tegument aggregates are described in WO 2006/110728.

Also provided are transgenic animals that include a GECI-encoding nucleic acid sequences described herein. "Animal" refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal in which one or more of the cells of the animal contain a heterologous nucleic acid. Methods for making transgenic animals have been described, for example, in Wagner et al. (1981, PNAS USA, 78:5016-5020); Stewart et al. (1982, Science, 217:1046-1048); Constantini et al. (1981, Nature, 294:92-94); Lacy et al. (1983, Cell, 34:343-358); McKnight et al. (1983, Cell, 34:335-341); Brinstar et al. (1983, Nature, 306:332-336); Palmiter et al. (1982, Nature, 300:611-615); Palmiter et al. (1982, Cell, 29:701-710); and Palmiter et al. (1983, Science, 222:809-814). Methods for making transgenic animals also are described in U.S. Pat. Nos. 6,175,057; 6,180,849; and 6,133,502.

One or more of the nucleic acid sequences, polypeptides, vectors or cells described herein, or combinations thereof, can be packaged into an article of manufacture (i.e., a kit) using containers, vials, or the like. For example, an article of manufacture can include (i) a nucleic acid sequence encoding a GECI, wherein the GECI has a sequence shown in SEQ ID NO: 2, SEQ ID NO:4, SEQ ID NO:6, SEQ ID NO:8 or SEQ ID NO:10, or a variant of those sequences as discussed above; (ii) a GECI polypeptide having a sequence shown in SEQ ID NO: 2, SEQ ID NO:4, SEQ ID NO:6, SEQ ID NO:8 or SEQ ID NO:10, or a variant of those sequences as discussed above; (iii) a vector comprising (i); (iv) a cell comprising (i); (v) a cell comprising (iii); or (vi) a cell comprising (ii). An article of manufacture as described herein can include any combination of (i)-(vi).

In addition, an article of manufacture as described herein can include one or more reagents, buffers, culture medium, neuronal or other type of cell, a G-protein coupled receptor (GPCR) polypeptide or a nucleic acid encoding a GPCR polypeptide, or an ion channel polypeptide or a nucleic acid encoding an ion channel polypeptide. An article of manufacture also can include instructions for use.

Methods of Using the Nucleic Acid and Polypeptide Compositions

The nucleic acid and polypeptide compositions described above, including, for example, vectors and cells containing such vectors, can be used in methods of screening for G-protein coupled receptor (GPCR) or ion channel agonists and antagonists. For example, a cell that expresses both a GPCR and one of the genetically encoded calcium indicators (GECI) described herein (e.g., a nucleic acid having the sequence shown in SEQ ID NO:1, SEQ ID NO:3, SEQ ID NO:5, SEQ ID NO:7 or SEQ ID NO:9 encoding a polypeptide having the sequence shown in SEQ ID NO: 2, SEQ ID NO:4, SEQ ID NO:6, SEQ ID NO:8 or SEQ ID NO:10, respectively) or a cell that expresses both an ion channel and one of the GECIs described herein can be contacted with an agent to be tested, and the level of fluorescence determined.

Generally, using the methods described herein, an increase in fluorescence indicates that the agent is a GPCR or ion channel agonist, while a decrease in fluorescence indicates that the agent is a GPCR or ion channel antagonist. As indicated herein, the GPCR or ion channel can be endogenous to the cell, or can be heterologous to the cell. If the GPCR or ion channel is heterologous to the cell, the nucleic acid encoding the GPCR or ion channel can be on the same or a different vector from the nucleic acid encoding the GECI or ion channel. Fluorescence is routinely determined in laboratories, and the level of fluorescence can be determined using any type of fluorometer.

Those skilled in the art understand that a determination of an increase or a decrease in fluorescence in the presence of an agent requires the use of an appropriate control. By way of example, one appropriate control can be measuring the level of fluorescence in a cell before and/or after a treatment (i.e., contact with an agent); another appropriate control can be measuring the level of fluorescence in the absence of a treatment (i.e., contact with an agent).

As used herein, an agent that can be screened in the methods described herein includes, for example, a polypeptide, an antibody (e.g., polyclonal or monoclonal; human or humanized) a small molecule, a nucleic acid molecule, a peptidomimetic, or any combination thereof. Nucleic acid molecules used in a method of screening as described herein can be, for example, an inhibitory nucleic acid molecule. Inhibitory nucleic acid molecules include, for example, a triplex forming oligonucleotide, an aptamer, a ribozyme, a short interfering RNA (siRNA), a micro-RNA (miRNA), or antisense nucleic acid. These types of inhibitory nucleic acid molecules are well known in the art and methods of designing them and making them also are well known in the art.

As is understood in the art, a G-protein coupled receptor (GPCR) refers to any member of a superfamily of receptors that mediates signal transduction by coupling with a G protein and is associated with a change in Ca2+ signaling and/or concentration. This class of GPCRs acts through the Gq type of G proteins, which activate a phospholipase C (PLC) pathway, resulting in the hydrolysis of phosphoinositides to generate two classes of different second messengers, diacylglycerol and inositol phosphates. Diacylglycerol activates certain protein kinase Cs (PKCs) and certain inositol phosphates stimulate the mobilization of calcium from intracellular stores.

Exemplary GPCRs include, but are not limited to alpha-1 adrenergic receptors (α1-AR), urotensin (UT) receptors, 5-HT2 and 5-HT6 serotonin receptors, hypocretin (orexin) receptors, histamine H1 receptors, bradykinin B1 and B2 receptors, bombesin BB2 receptors, P2Y purinergic receptors, acetylcholine receptors (e.g., M1, M3 and M5), mGluR5 glutamate receptors, vasopressin V2 and V1 receptors, angiotensin AGTR1 receptors, cholecystokinin CCKAR and CCKBR receptors, endothelin ENDRA receptors, ghrelin GHSR1a receptors, melatonin MTNR1A receptors, neurotensin NTSR1 receptors, platelet-activating factor PTAFR receptors, and prolactin releasing peptide receptor PRLHR receptors.

It is also possible to study Gs- and Gi-coupled receptors by co-expressing a cAMP-gated Ca2+ channel (Airan et al., 2009, Nature, 458(7241):1025-1029). This is carried out by taking advantage of the promiscuous G-protein G15/16 (Zhang et al., 2003, J Biomol Screen, 8(5):571-577), or by using chimeric G-proteins (Hsu and Luo, 2007, Am J Physiol Endocrinol Metab., 293(4):E1021-E1029). Such receptors include, but are not limited to, G-coupled 5-HT6 and 5-HT7 serotonin receptors, Gi-coupled GABA-B, histamine H3, and mGluR2/4 glutamate receptors.

As is understood in the art, an ion channel refers to any member of a superfamily of proteins that mediate cation or anion conductance into a cell, either through molecule binding (ligand-gated ion channels), membrane depolarization (voltage-gated ion channels), temperature stimulus (temperature-gated ion channels), force stimulus (force-gated ion channels), light stimulus (light-gated ion channels), pressure stimulus (pressure-gated ion channels), or other stimuli. Suitable ion channels for use with the GECIs described herein typically are calcium ion channels.

Exemplary ligand-gated calcium channels include, but are not limited to, AMPA (α-amino-3-hydroxy-5-methyl-4-isoxazolepropionic acid) receptors including iGluR1, iGluR2, iGluR3, iGluR4; NMDA (N-methyl-D-aspartate) receptors including NR1 and NR2; kainate receptors including iGluR5, iGluR6, iGluR7, KA1, and KA2; nicotinic acetylcholine receptors including alpha9, alpha10, alpha7, alpha8, alpha2, alpha3, alpha4, alpha6, beta2, beta4, beta3, alpha5, alpha1, beta1, gamma, delta, or epsilon nicotinic acetylcholine receptor subunits; P2X receptors; P2Y receptors; IP3 receptors; ryanodine receptors; two-pore calcium channels; and sperm cation channels. Representative voltage-gated calcium channels include, but are not limited to, L-type, N-type, P/Q-type, and R-type voltage-gated calcium channels such as CaV1.1, CaV1.2, CaV1.3, CaV1.4, CaV2.1, CaV2.2, CaV2.3, CaV3.1, CaV3.2, and CaV3.3. Exemplary temperature-gated calcium channels include, without limitation, transient receptor potential (TRP) channels including TRPC, TRPV, TRPA, TRPM, TRPP, TRPML, and TRPN channels. Representative light-gated calcium channels include channelrhodopsin-2 (ChR2) and mutants thereof. Some of these calcium ion channels, such as the TRP channels, respond to other stimuli such as force and/or pressure.

The nucleic acid and polypeptide compositions described above, including, for example, expression vectors and cells containing such expression vectors, can be used in methods of determining the calcium ion status of a cell. In addition, the nucleic acid and polypeptide compositions described above can be used in methods of monitoring neuronal activity. As discussed in more detail below, neuronal activity can be monitored in neuronal cells that are expressing a nucleic acid encoding a GECI polypeptide as described herein (e.g., a nucleic acid encoding a polypeptide having the sequence shown in SEQ ID NO: 2, SEQ ID NO:4, SEQ ID NO:6, SEQ ID NO:8 or SEQ ID NO:10), and detecting the fluorescence emitted by the cells. Neuronal activity can be natural (e.g. neurons in the brain of an animal that is behaving, or a brain slice exhibiting spontaneous activity), or can be elicited by a chemical stimulus, an electrical stimulus, or another type of stimulus. A chemical stimulus can include a drug or combination of drugs, a toxin, a neurotransmitter, or any other compound. An electrical stimulus can be delivered, for example, from an extracellular electrode, or from an intracellular electrode, a magnetic resonance imaging (MRI) device, or any other type of electrical stimulus.

The neuronal cells can be contacted with the stimulus in vitro (e.g., in cell culture) or in vivo (e.g., in an animal such as, without limitation, a mouse, a worm, a rat, or a fly). Neuronal activity is used herein as an example, but those skilled in the art would understand that the activity of other cells types can be examined. For example, the activity of muscle cells, cardiomyocytes, or astrocytes and other glial cells can be evaluated using the compositions and methods described herein. Other cell types that can evaluated using the compositions and methods described herein include bacteria, single-cell pathogens, or cells in nematodes, insects, arachnids, and other animals.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Molecular Biology

A third-generation, SIV-based, pro-lentiviral vector was used (Hanawa et al., 2004, Blood, 103:4062-9). Sequences containing a 476-bp human synapsin-1 promoter element, GCaMP3 coding region, an EMCV internal ribosome entry site, a nuclear localization tag fused to mCherry, a woodchuck hepatitis post-transcriptional regulatory element, and a rabbit beta-globin poly-adenylation signal were inserted between LTRs. GCaMP variants were constructed by PCR of the coding region using mutagenic primers. Mutated coding regions were then inserted into the pro-lentiviral vector by ligation-independent cloning.

Example 2—Neuronal Culture

Experiments were conducted according to National Institutes of Health guidelines for animal research and were approved by the Janelia Farm Research Campus Institutional Animal Care and Use Committee. Neonatal rat pups were sacrificed and hippocampi were dissected and dissociated in papain (Worthington, ~10 U/hippocampal pair) in neural dissection solution (10 mM HEPES pH 7.4 in HBSS) for 25 min at 37° C. Following trituration with a Pasteur pipette and passage through 40-µm strainer, cells were plated at a density of $2.25 \times 10^5$ viable cells/well in 150 µL plating medium (28 mM glucose, 2.4 mM $NaHCO_3$, 100 µg/mL transferrin, 25 µg/mL insulin, 2 mM L-glutamine, penicillin/streptomycin, 10% fetal bovine serum in MEM) in 24-well glass-bottom plates (Mattek, #1.5 glass coverslips). Wells were pre-coated with 100 µL Matrigel (1:50 dilution in MEM, BD Biosciences), which was aspirated immediately before plating cells. After 1 h at 37° C., 1 mL plating medium was added to wells. After 16 h, plating medium was replaced with 1 mL growth medium (28 mM glucose, 2.4 mM sodium bicarbonate, 100 µg/mL transferrin, B-27 supplement (1×, Invitrogen), 500 µM L-glutamine, penicillin/streptomycin, 5% fetal bovine serum in MEM). A mouse monoclonal anti-GAD67 antibody (Millipore) was used to stain fixed cultures.

Example 3—Lentiviral Particle Production and Infection

A pro-lentiviral construct was combined packaging and coat pseudotyping DNA constructs (pCAG-SIVgprre, pCAG4-RTR-SIV, pCMV-VSV-G; Hanawa et al., supra; Stewart et al., 2003, RNA, 9:493-501) and transfected into $32 \times 10^6$ HEK293T/17 cells (ATCC) cultured in DMEM and 10% fetal bovine serum in 10-cm plates. After 72 h, supernatant was collected (6 mL) and passed through a 0.45-µm filter. For each well of a 24-well plate, 0.5 mL of lentivirus was combined with 0.5 mL of growth medium and incubated for 16 h at 37° C. Medium was exchanged with 1 mL growth medium supplemented with 4 µM AraC to inhibit glial proliferation. Lentiviral particles were used in a biosafety level 2 laboratory.

Example 4—Stimulus and Imaging

Neuronal culture growth medium was exchanged 3 times with imaging buffer (145 mM NaCl, 2.5 KCl, 10 mM glucose, 10 mM HEPES pH 7.4, 2 mM $CaCl_2$, 1 mM $MgCl_2$) and imaged in 500 µL of imaging buffer and drugs (10 µM CNQX, 10 µM (R)-CPP, 10 µM gabazine, 1 mM (S)-MCPG, Tocris). Ionomycin (Sigma) used for maximum calcium response measurements was dissolved in DMSO. A Grass S48 Stimulator (Grass Technologies) was used. For GCaMP imaging, the microscope was an Olympus IX81 with 10× (0.4 NA) air objective lens, Prior H117 ProScan II motorized stage, Andor Technology EMCCD camera (DU897_BV, 512×512 resolution, 35 frames/s, 100 electron multiplying gain, 1× pre-amp gain, −60° C.), Cairn OptoLED illumination system, and Chroma ET-GFP and ET-TxRed filter sets. The imaging system was controlled by custom journals written in MetaMorph software (version 7.7.5, Molecular Devices), which controlled data acquisition boards (USB-6501, USB-9263, National Instruments). The stimulation and image timing was controlled as a slave using another data acquisition board (USB-6259, National Instruments) and Ephus software (Suter et al., 2010, Front Neural Circuits, 4:100). The imaging computer was from PSSC Labs (PowerStation Duo 12600, dual Intel X5650 Hex Core 2.66 GHz processors, 96 GB RAM). For ArchWT-GFP imaging, the same system was used except with a 60× (1.45 NA) oil objective lens; 0.25× demagnifier; high-speed, Andor Technology EMCCD camera (DU860_BV, 128×128 resolution, 500 frames/s, 1000 electron multiplying gain, 1× pre-amp gain, 60° C.); CrystaLaser 638 nm, 100 mW laser; Chroma custom filter set (640/8 nm excitation, 640 nm longpass dichroic, 675 nm bandpass emission).

APs (83 Hz) were evoked by field stimulation with a Grass Technologies S48 stimulation unit and a custom-built 24-well cap stimulator with pairs of parallel platinum wires. The microscope was an Olympus IX81 with a 10× (0.4 NA) air objective lens and EMCCD camera (Andor 897, 512×512 pixels, 35 frames/s), Cairn OptoLED illumination system, and GFP (Ex:470/40; Di:495LP; Em:525/50) and TxRed (Ex: 560/40; Di:585LP; Em:630/75) filter sets. The field of view was 800 μm×800 μm. Images were background subtracted (mean of 5% lowest pixel values). Responses were quantified for each cell as change in fluorescence divided by baseline fluorescence measured one second prior to stimulation. Signal-to-noise ratio (SNR) was quantified as peak response over the standard deviation.

Control experiments varying stimulation voltage, frequency, and pulse width insured suprathreshold stimulation of neurons. Voltage imaging using the ArchWT-GFP archaerhodopsin-based voltage sensor confirmed that individual pulses (1 ms, 40 V, 83 Hz) reliably triggered single APs. The imaging and stimulation system was controlled by custom scripts written in MetaMorph software (Version 7.7.5, Molecular Devices) and Ephus software (ephus.org on the World Wide Web).

Example 5—Image Analysis

Analysis was implemented in MATLAB (release 2010a, MathWorks). For GCaMP fluorescence transients, background subtraction was applied through subtraction of the mean of the lowest 5% intensity values. F0 was defined as the mean of fluorescence 10 frames prior to stimulus onset. The signal-to-noise ration (SNR) was computed as the ratio between the peak fluorescence response amplitude and the standard deviation of the fluorescence trace 10 frames before stimulus onset. For voltage imaging, activity-based segmentation of pixels was employed.

Example 6—Calcium Titrations In Vitro pRSET-A plasmids containing GCaMP variants were used to express protein in T7 Express *E. coli* cells (New England Biolabs) using 100 mL of ZYM-5052 auto-induction media and ampicillin at 30° C. for 48 h. Cells were lysed in B-PER (Thermo Scientific), 1 mg/mL lysozyme, 15 U/mL DNase at 22° C. for 30 min. After clearing, variants were purified using $Ni^{2+}$-charged Profinity IMAC resin (Bio-Rad). Columns were washed with 20 mM Tris pH 8, 300 mM NaCl, 1 mM imidazole followed and then with 20 mM Tris pH 8, 500 mM NaCl, 10 mM imidazole. Variants were eluted in with 20 mM Tris pH 8, 100 mM NaCl, and 100 mM imidazole. Eluted protein concentrations ranged from 9-67 μM. Eleven-point calcium titrations were done using EGTA-buffered $Ca^{2+}$ solutions, similar to the protocol of the Calcium Calibration Buffer Kit #1 (Life Technologies). Green fluorescence intensities (excitation 485 nm, 5 nm bandpass; emission 510 nm, 5 nm bandpass) were measured using a Safire2 plate reader (Tecan).

Example 7—Imaging Mouse V1 Neurons

Visual stimuli, imaging, and in vivo cell-attached recording for mouse experiments have been described (Akerboom et al., 2012, J. Neurosci., 32: 13819-40). Constructs used to produce AAV included pGP-AAV-syn-GCaMP-WPRE and the Cre recombinase-activated construct pGP-AAV-syn-flex-GCaMP-WPRE. AAV virus was injected slowly (30 nL in 5 minutes) at a depth of 250 μm into the primary visual cortex (two sites, 2.5 and 2.9 mm lateral from the lambda suture) of C57BL/6J mice (1.5-2 months old). For dendritic imaging, sparse labeling was achieved by injecting a mixture of diluted AAV-syn-Cre particles and high titer, Cre-dependent GCaMP6s virus. This produces high levels of GCaMP6 expression in a small subset of neurons, defined by Cre expression. The dilution factor of the AAV-syn-Cre virus was adjusted empirically so that ~3-5 neurons were labeled with GCaMP6 in a 250 μm×250 μm×250 μm volume.

After 1-4 weeks of expression, mice were anesthetized using isoflurane (3% for induction, 1.5-2% during surgery) and a circular craniotomy (2-3 mm diameter) was made above V1 (centered 2.7 mm lateral from the lambda suture). In some cases, OGB1-AM (Invitrogen) was injected into V1 in mice without GCaMP expression. For acute experiments, the craniotomy was covered with agarose (1-1.3%) and a round glass coverslip (Warner Instruments; 5 mm diameter; #1 thickness) was cemented to the skull to reduce motion of the exposed brain. A custom titanium head post was fixed to the skull using black dental cement (Contemporary Ortho-Jet). For simultaneous imaging and cell-attached recording, the exposed brain was covered with ~1 mm thick agarose (1.3%) without a coverslip. For chronic imaging experiments, the imaging window was constructed from two layers of microscope coverglass. A larger piece (Fisher, #1 thickness) was attached to the bone and a smaller insert (#2 thickness) was fitted snugly into the craniotomy. Imaging experiments were started ~1-2 weeks after chronic window implantation. For imaging, mice were anesthetized with 0.5% isoflurane and sedated with chlorprothixene (20-40 μL at 0.33 mg/ml, i.m.).

Imaging was performed using a custom-built two-photon microscope (designs available at research.janelia.org/Svoboda) equipped with a resonant galvo scanning module (Thorlabs), controlled by ScanImage (scanimage.org). The light source was a Mai Tai femtosecond pulsed laser (Spectra-Physics) running at 940 nm for GCaMP variants and 800 nm for OGB1-AM. The objective was a 16× water immersion lens (Nikon, 0.8 NA, 3 mm working distance). The power used was 35-50 mW for full field imaging (FIG. 9) and 20-30 mW for high zoom imaging (FIGS. 9-10).

Images (512×512 pixels, 250 μm×250 μm) were collected at 30 Hz and temporally binned 2× online to give 15 Hz effective sampling rate. In vivo cell-attached recording was performed using glass pipettes (~5-7 MΩ) filled with solution containing the following (in mM): 125 NaCl, 5 KCl, 10 glucose, 10 HEPES, 2 $CaCl_2$, 2 $MgSO_4$, and 0.1 Alexa Fluor 594). Signals were amplified using an AxoPatch 200B amplifier (Molecular Devices), filtered at 5 kHz, and digitized at 10 kHz. Spikes were recorded using current clamp mode. Images (256×256 pixels, 30 μm×30 μm) were acquired at 60 Hz. The frame trigger pulses of ScanImage 4.0 were also recorded and used offline to synchronize individual frames to electrophysiological recordings. For dendritic imaging experiments, images (512×512 pixels, 30 μm×30 μm) were acquired at 30 Hz. Images were taken from apical or basal dendritic segments with multiple spines in one focal plane. At the end of each imaging session, z-stacks of the recorded dendrite were acquired at 0.5 μm spacing. The coordinates of the imaged dendrites relative to the parent somata were recorded and used in chronic experiments to re-identify the same dendrites and spines weeks later. The orientation, curvature, and the branching pattern of the dendrites together with the constellation of spines further helped to precisely identify the same FOV. The moving grating stimuli were generated using the Psychophysics Toolbox in MATLAB. Each stimulus trial consisted of a 4 s blank period (uniform gray at mean luminance) followed by a 4 s drifting sinusoidal grating (0.05 cycles per degree, 1 Hz temporal frequency). Typically, 8 drifting directions were used (separated by 45 degrees) and 5 trials were recorded for each direction, giving a total of 40 stimulus trials per recording session (320 s recording time). The gratings were presented with an LCD monitor (30×40 cm), placed 25 cm in front of the center of the right eye of the mouse. The monitor subtended an angle of 38° horizontally and ~20° to ~38° vertically around the eye of the mouse. For cell-attached recording, a smaller LCD monitor (12×16 cm) was used and placed ~10 cm in front of the right eye. After establishment of a low-resistance seal (15-50 MΩ), the orientation, spatial and temporal frequency of the stimuli were quickly optimized for individual neurons using recorded spikes. During simultaneous imaging and electrophysiology, the optimal grating stimulus was repeatedly played (duration 2 s, interstimulus interval 6 s), and the contrast of the stimulus grating was adjusted online to maintain moderate spike rates.

Figure 17A:
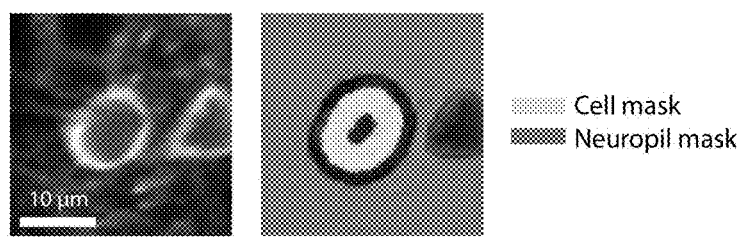
FIG. 17A shows a GCaMP6s labeled cell targeted for cell attached recording (left) and regions where cell (green) and neuropil (red) fluorescence were measured (right).
Figure 17B:
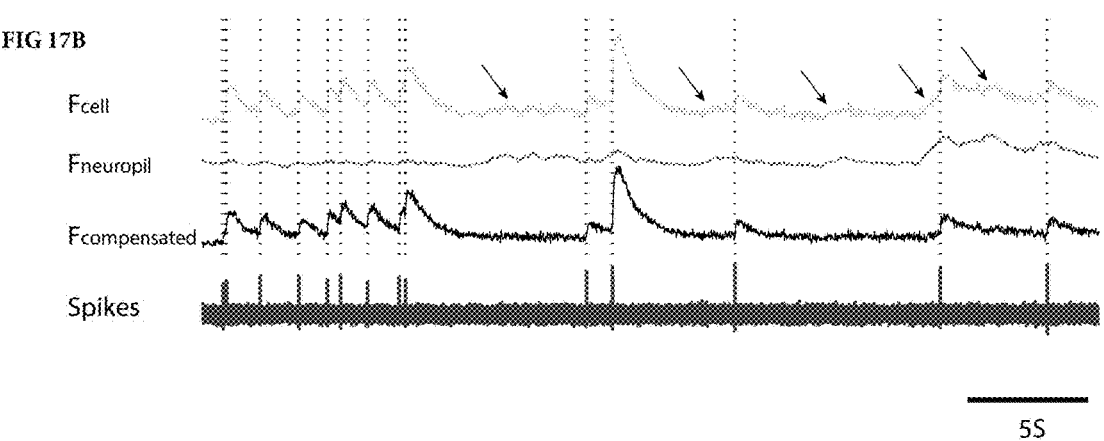
FIG. 17B shows, from top to bottom, averaged fluorescence of the cell region, average fluorescence of surrounding neuropil region, estimated true fluorescence of the cell after neuropil compensation, and simultaneously recorded spikes. Fluorescence changes not related to spikes (arrows) were removed after neuropil subtraction.

Mechanical drift in the imaging plane was corrected using the TurboReg plug-in in ImageJ. All remaining analyses were performed in MATLAB. Regions-of-interest (ROIs) corresponding to visually identifiable cell bodies were selected using a semi-automated algorithm (FIG. 16). For GCaMP, ring-shaped ROIs were placed at the cytosolic regions of the cells (excluding the nucleus; GCaMP expression is typically restricted to the cytoplasm). For OGB1-AM, circular ROIs covering the whole soma were used. For long-term GCaMP imaging, baseline fluorescence images of multiple sessions were inspected manually, and only the cells that could be clearly identified in all imaged sessions were included in the analysis. The fluorescence time course of each cell was measured by averaging all pixels within the ROI, with a correction for neuropil contamination. The fluorescence signal of a cell body was estimated as $F_{cell\_true}(t) = F_{cell\_measured}(t) - r \cdot F_{neuropil}(t)$, with $r=0.7$. The neuropil signal $F_{neuropil}(t)$ surrounding each cell was measured by averaging the signal of all pixels within a 20 μm region from the cell center (excluding all selected cells). Cell attached recording confirmed that neuropil-compensated fluorescence changes reflect action potentials in single neurons (FIG. 17). The neuropil correction was not applied for dendritic imaging experiments due to a low background contamination resulting from sparse labeling. The $\Delta F/F_0$ was calculated as $(F-F_0)/F_0$, where $F_0$ is the baseline fluorescence signal averaged over a 2 s period immediately before the start of visual stimulation. Visual response of each trial was measured as $\Delta F/F_0$ averaged over the stimulus period (4 s). Visually responsive neurons were defined as cells showing significant-stimulus related fluorescence change (ANOVA across blank and eight direction periods, p<0.01) with an average $\Delta F/F_0$ at preferred orientation greater than 6%. The orientation selectivity index (OSI), tuning width, and direction selectivity index (DSI) were calculated for visually responsive cells. For simultaneous imaging and cell-attached recording, ring-shaped ROIs were placed at the cytosolic regions of the cells. Fluorescence transients at the soma were caused by action potentials, with little contribution from subthreshold activity.

To quantify single AP detection efficiency, the spike trace was searched for isolated 1 AP events where nearby APs were at least 1 s away. Segments of fluorescence traces ~0.17 s (10 frames) before and 1 s (60 frames) after the $i^{th}$ 1 AP event (1AP calcium traces) were taken to form 70-dimensional vectors, $f_i$. From the same fluorescence recording, segments of noisy traces, m (i.e., 0 AP traces) were taken from periods where no AP was detected for at least 2 s. The average of all 1 AP traces was used as a template vector, $f_{template} = \Sigma_i f_i/N$. The template vector was then mean removed and normalized to create a unit vector $\hat{f}_{template}$. The vector projection of $f_i$ or $n_i$ along the direction of $\hat{f}_{template}$ was calculated to obtain a scalar number $f_i = \langle f_i, \hat{f}_{template} \rangle$ or $n_i = \langle n_i, \hat{f}_{template} \rangle$ for each trace. The AP detection threshold was taken as the 99th percentile of all m values (i.e., 1% false positive), and the percentage of the $f_i$ values above the detection threshold was the AP detection efficiency.

For spine images (FIG. 10), circular ROIs were placed at individual dendritic spines to measure spine calcium signal and the corresponding $\Delta F/F_{0\_spine}$. To minimize contamination from back-propagating action potentials (BAPs), the recordings were taken from 'silent cells' (~40% of cells) showing few or no APs in response to a standard set of grating stimuli. Occasional spontaneous BAP related calcium signals that invaded the imaged spines were removed using the following method (FIG. 14). First, a region covering the entire parent dendritic shaft (excluding all spines) was drawn manually for each recorded dendritic segment to estimate BAPs related global dendritic signal, d(t), and the corresponding $\Delta F/F_{0\_dendrite}$. Plotting $\Delta F/F_{0\_spine}$ against $\Delta F/F_{0\_dendrite}$ reveals two components of spine signals, a BAP related component and a spine specific component. The BAP related component was removed from the spine signals by subtracting a scaled version of the dendritic signal, $\Delta F/F_{0\_spine\_specific} = \Delta F/F_{0\_spine} - \alpha \cdot \Delta F/F_{0\_dendrite}$, with the $\alpha$ factor determined using robust regression (MATLAB function 'robustfit.m') of $\Delta F/F_{0\_spine}$ vs. $\Delta F/F_{0\_dendrite}$ (the slope of the fitted line in FIG. 14B). The visual responsiveness (ANOVA, p<0.01) and the OSI of individual spines were calculated using BAP removed spine signals. Active spines were defined as spines showing at least 3 spine-specific (i.e., BAP independent) calcium events during the 5 minute imaging session, with an event defined as an episode of the calcium signal that crosses 3 SD of the baseline noise for at least three consecutive frames (~50 ms).

Analysis of populations of dendritic spines (FIG. 11) was restricted to cells with tuned somatic responses. The stimulus contrast was lowered to reduce action potential-related dendritic signals (average $\Delta F/F_0$ in dendritic shafts at the preferred orientations was 32%, 80%, 16%, 15%, 12% for cells 1 through 5, corresponding to stimulus contrast 10-40%, 5-20%, 10-40%, 20-40%, 20-40%). The orientation preference of dendritic shafts was always consistent with the soma. These dendritic signals were removed from spine signals using the subtraction approach described above. The subtraction algorithm was verified by measuring the trial-to-trial correlation between dendritic shaft signal and action potential subtracted spine signals. 20.3% of visually responsive spines ($\Delta F/F > 10\%$) still showed significant trial-to-trial correlation with dendritic shaft responses compared to shuffled controls (p<0.01). This could reflect synchronously active pre-synaptic cells, or imperfect action potential signal subtraction. Because we were unable to distinguish between these possibilities, these spines were excluded from further analysis. In two cells (cell 4 and cell 5), shorter stimulus durations (1s) were used and larger numbers of trials (15 trials per orientation) were collected. In these cells, trials with detectable dendritic response ($\Delta F/F_0 > 6\%$) were excluded from the analysis.

For imaging input to GABAergic interneurons (FIGS. 12 and 15), Cre-dependent GCaMP6s AAV was injected (30 nl) into the visual cortex of PV-IRES-Cre mice. Individual somata (FIG. 15) and dendritic segments could be recognized (FIGS. 12G and 12H, total length of imaged dendrite: 2.86 mm), but it was difficult to track individual dendrites over long distances due to the high labeling density. Sparse labeling was achieved by injecting mixtures of low titer AAV-syn-Cre and high titer AAV-syn-Flex-GCaMP6s in wild type mice. Although this approach labeled both pyramidal and GABAergic neurons, labeled GABAergic cells could be identified based on absence of dendritic spines. Post hoc immunolabeling further identified the imaged cells. Orientation tuning of dendrites were mapped using the standard stimulus set (8 directions, 5-10 trials, 8 s inter trial interval) at high contrast. The stimulus duration was reduced to 2 s (i.e., 6 s blank period). Imaged dendrites were traced using 'Simple neurite tracer' in ImageJ. The program outputs a 1D sequence of coordinates traversing a dendrite and a 2D mask covering the traced dendrite, which were used to define ROIs along the dendrite (size, 1.5 μm of dendritic length; spacing, 1 μm). Visual responsiveness and orientation selectivity were computed for individual dendritic ROIs. Because synaptic signals and action potential signals were mixed in the same compartment, no attempt was made to subtract action potential-related signals, which were relatively weak and restricted to the proximal parts (<100 μm) of interneurons.

Example 8—Reagent Distribution

DNA constructs and AAV particles with GCaMP6 variants were deposited for distribution at Addgene (addgene.org on the World Wide Web) and the University of Pennsylvania Vector Core (med.upenn.edu/gtp/vectorcore on the World Wide Web), respectively.

Example 9—GCaMP Variants and Methods of Screening GCaMP Variants

Variants were made by mutating the GCaMP3 coding region by site-directed mutagenesis at selected positions in an SIV-based lentiviral expression vector (FIG. 1B). The large size and presence of recombinogenic repeat sequences in the lentiviral vector made PCR-based mutagenesis difficult. Instead, mutagenesis was carried out by mutation of coding regions separately and subsequent sequence assembly with the lentiviral vector. Individual variants were then packaged in lentiviral particles using tissue culture cells. Sufficient viral titer could be obtained without concentration of viral particles, and use of lentiviruses allowed for transduction of both dividing and post-mitotic cells. Dissociated neonatal rat hippocampal cells were infected at 3 days in vitro (DIV) in 24-well, glass-bottom plates for 16 hours. Glial proliferation was inhibited on day 4 by addition of the nucleotide analogue, AraC. Neuron-selective GCaMP3 variant expression was achieved using a 476-bp human synapsin-1 promoter element. Additionally, a nuclear localization signal (nls) tagged red fluorescent protein was co-expressed in neurons using an IRES-nls-mCherry sequence (FIG. 1B, 1C). Red fluorescence was used both for image segmentation and GCaMP3 variant expression normalization. Hippocampal cultures were diverse in neuronal composition and included inhibitory GABAergic neurons and excitatory glutamatergic neurons.

At 16-18 DIV, variants were tested by field stimulation of neuronal cultures and imaging of fluorescence responses. Growth medium was exchanged with imaging buffer in a standard volume. A plate was placed on the screening platform, and a custom-built 24-well cap stimulator was fitted into wells such that pairs of parallel platinum wires extended into the buffer (FIG. 1D). Temperature was monitored using thermocouples in two of the wells. Imaging was initiated by an incoming trigger. Pairs of wires were then independently controlled to emit field pulses (FPs) from a power source. Baseline images were captured for 1 s and then stimulus was applied. Images were captured using a fully automated inverted microscope, a motorized stage, and an EMCCD camera (FIG. 1E). The trigger was initiated by software (MetaMorph, Molecular Devices), and image timing and electrical stimulation parameters were then controlled as a slave by a separate custom software package (Ephus, Suter et al., supra). Illumination was provided by LEDs with optical feedback to maintain stability and filter sets in a motorized turret.

Figure 3B:
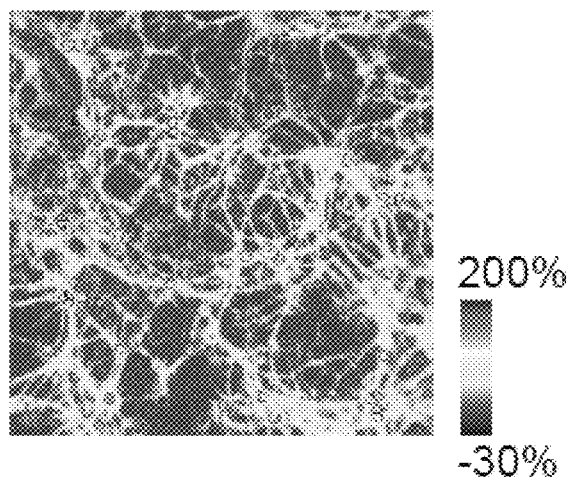
FIG. 3B shows the 10AP ΔF/F0 response map.
Figure 3C:
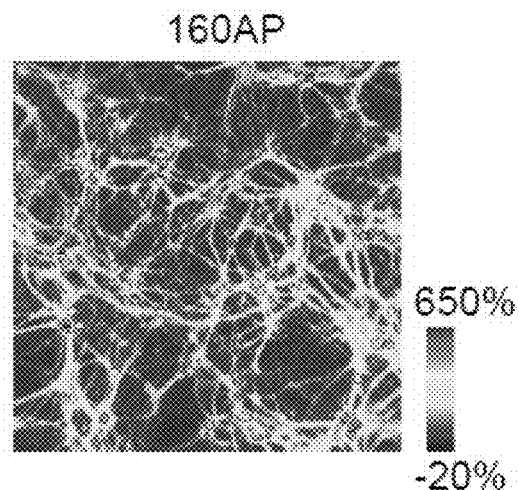
FIG. 3C shows the 160AP ΔF/F0 response map.
Figure 3D:
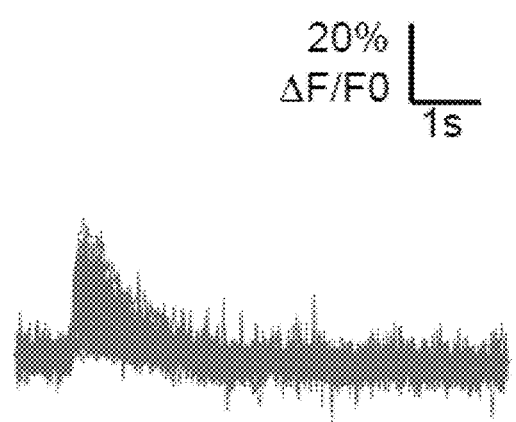
FIG. 3D shows the 3AP ΔF/F0 traces for ROI (gray; Median trace (red))
Figure 3E:
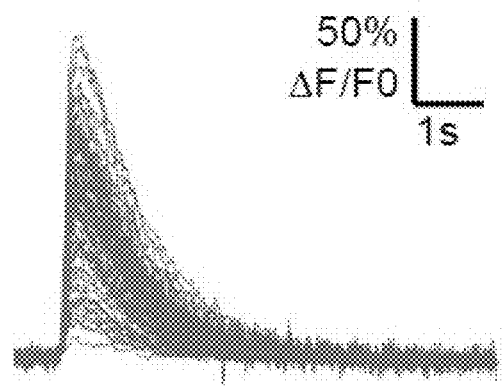
FIG. 3E shows the 10AP ΔF/F0 traces.
Figure 3F:
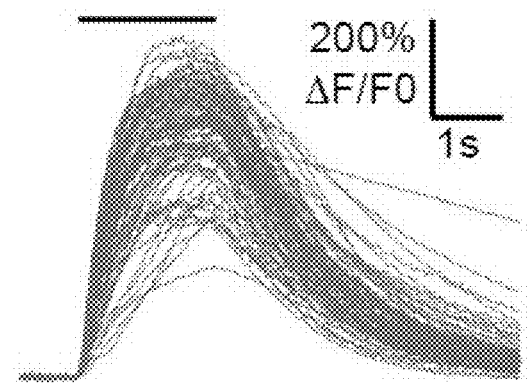
FIG. 3F shows the 160AP ΔF/F0 traces.

Fields of view (FOVs) were located from a predetermined list of stage coordinates, corresponding to centers of each well. An imaging-based autofocusing routine was applied using an algorithm based on nearest neighbor pixel contrast in the mCherry channel (Brenner et al., 1976, J. Histochem. Cytochem., 24:100-11). To focus on mCherry-tagged nuclei with 2-μm precision, four focus loops of increasing search accuracy were used. The variation in the glass bottom of wells ranged up to 500 μm in z position across a plate. After focusing, reference mCherry, GCaMP, and bright field images were acquired. Then a trigger was sent to simultaneously initiate imaging and stimulus and imaging timing. Image timing data from the camera, temperature from thermocouples, LED light levels, stimulus current, and stimulus voltage were recorded at 10 kHz. Buffer temperature was ~30° C. Fluorescence image streams (35 frames/s, 250 frames) were captured using a cooled EMCCD camera controlled by MetaMorph. Reference images were also captured after stimuli. To assay GECI performance at cellular resolution, regions of interest (ROI) corresponding to nls-mCherry- and GCaMP-positive neuronal cell bodies were identified using custom software. To define ROIs, a raw mCherry image was low-pass filtered with a circular kernel roughly the size of a cell nucleus (FIG. 2A, 2B). Putative locations of cells were determined as the local maxima of the filtered image whose intensity crossed an adaptively defined threshold. Based on these 'seed' locations, a Voronoi diagram was drawn to cut the image into multiple sub-regions (FIG. 2C, Jones et al., 2005, Proc. First Intern. Conf. Computer Vision for Biomedical Image Applications, Springer-Verlag, pp 535-43). Adaptive thresholding was performed on the GCaMP and mCherry image within each sub-region to define pixels that belong to the cytosolic and nuclear ROIs, respectively (FIG. 2D). Averaged baseline GCaMP and mCherry fluorescence was measured within each cytosolic or nuclear ROI, and cells were excluded if the average mCherry level did not reach a predefined threshold (FIG. 2E). ROIs that touched the boundary of the image were also excluded. Examples of $\Delta F/F0$ responses in segmented neuronal cell bodies are shown in FIG. 3A, 3B, 3C. Fluorescence traces over time exhibited variable ΔF/F0 responses across different ROI (FIG. 3D, 3E, 3F). Possible sources of neuron-to-neuron variability included neuronal subtype diversity, differential electrical stimulation, connectivity differences, and variations in segmentation accuracy.

Figure 4A:
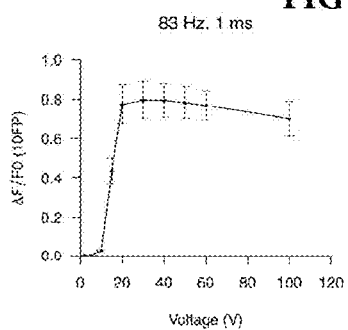
FIG. 4A shows the voltage dependency of GCaMP3 ΔF/F0 (10FP) response at 2, 5, 10, 15, 20, 30, 40, 50, 60, 100 V and 83 Hz and 1 ms pulse width (median±sem).
Figure 4B:
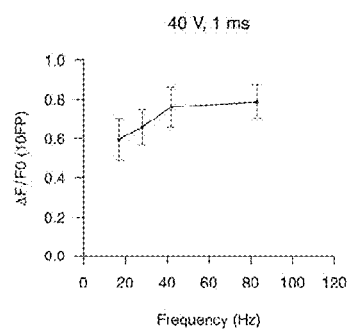
FIG. 4B shows the frequency dependency at 17, 28, 42, 83 Hz and 40 V and 1 ms pulse width.
Figure 4C:
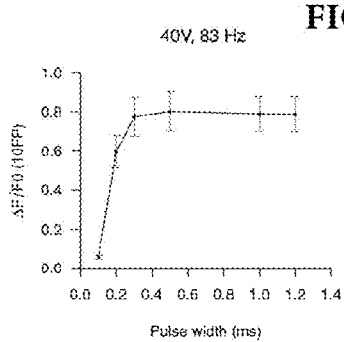
FIG. 4C shows the stimulus pulse width dependency at 0.1, 0.2, 0.3, 0.5, 1, 1.2 ms and 40 V and 83 Hz.
Figure 4D:
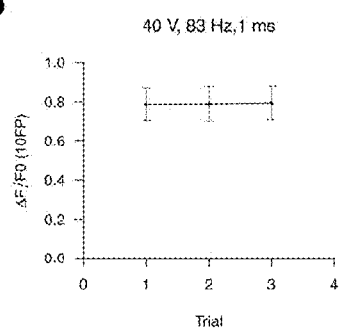
FIG. 4D shows the trial dependency after ~1-min intratrial intervals.
Figure 4E:
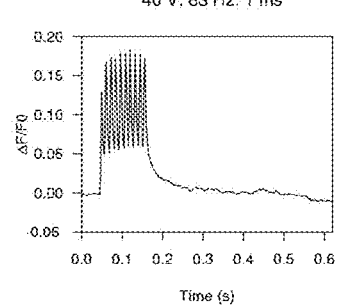
FIG. 4E is the voltage imaging showing the ΔF/F0 (10FP) response of the ArchWT-GFP voltage sensor at 40 V, 83 Hz, and 1 ms pulse width.

Stimulus parameters were optimized using GCaMP3 by varying field pulse current, frequency, and width. The ΔF/F0 response to 10FP in segmented neuronal cell bodies reached a maximum at 40 V current for a given pulse frequency and pulse width (FIG. 4A). It reach a maximum at 83 Hz frequency for a given pulse voltage and width (FIG. 4B). Finally, it reached a maximum at 500 μs width for a given pulse voltage and frequency (FIG. 4C). The response remained virtually unchanged through 3 trials spaced ~1 min apart (FIG. 4D). Based on these results, parameters were fixed at 40 V, 83 Hz, and 1 ms width to insure suprathreshold stimulation. These parameters also were used to stimulate fluorescence responses from the archaerhodopsin-3-based voltage sensor (ArchWT-GFP; FIG. 4E; Kralj et al., 2012, Nat. Methods, 9:90-5) to confirm that action potentials were evoked. Red laser illumination (638 nm, ~500 W/cm$^2$, FIG. 1E) and a high-speed EMCCD camera (500 frame/s) were used. With these parameters, 10FP evoked 10AP (FIG. 4E). In screening, stimulus trains of 1, 2, 3, 5, 10, 20, 40, 80, and 160AP were delivered with an intra-stimulus interval of ~20 s. Stimulus order was kept constant. After 160AP stimulus, a maximum calcium response was measured after addition of 20 mM CaCl$_2$ and 10 μM ionomycin.

Figure 5A:
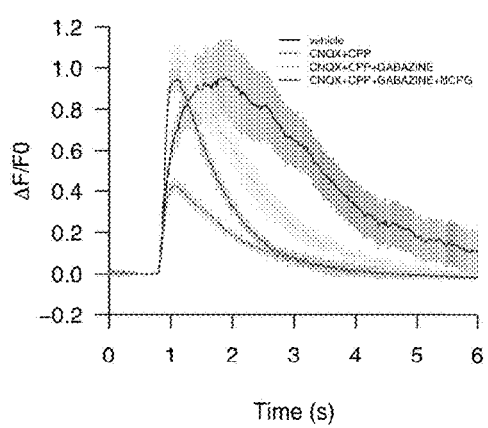
FIG. 5A shows the ΔF/F0 (10AP) response over time with imaging buffer alone (vehicle, black); ionotropic glutamatereceptor blockers (CNQX+CPP, red); ionotropic glutamate and GABA receptor blockers (CNQX+CPP+GABAZINE, green); ionotropic glutamate, GABA, and metabotropicglutamate receptor blockers (CNQX+CPP+GABAZINE+MCPG, blue); (median±sem).
Figure 5B:
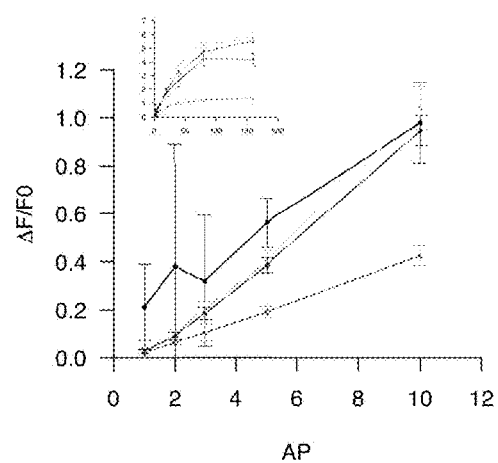
FIG. 5B shows the ΔF/F0 response after stimulation with 1, 2, 3, 5, 10AP (inset: 1, 2, 3, 5, 10, 20, 40, 80, 160AP).

Neuronal cultures formed functional networks. To control for network variability across wells, we sought to isolate individual neuronal responses from network influences by using neurotransmitter receptor inhibitors, including AMPA and NMDA glutamatergic receptors blockers CNQX and CPP (10 μM, FIG. 5A). Without these antagonists, the variability and magnitude of responses were relatively large (FIG. 5B), likely reflecting variable recurrent excitation in networks formed in culture. The glutamatergic antagonists reduced variability. Consistent with the presence of inhibitory GABAergic neurons, addition of a GABA$_A$ receptor antagonist, gabazine (10 μM), disinhibited the GCaMP3 ΔF/F0 response to 10AP stimulus by doubling it (FIG. 5A). A slow component of the GCaMP3 response was blocked by MCPG (1 mM). This metabotropic glutamate receptor blocker can inhibit G$_q$-mediated activation of intracellular calcium release. CNQX, CPP, gabazine, and MCPG were thus used together in screening to dampen variability due to network effects and intracellular calcium release and to widen the dynamic range of the calcium response.

Figure 6A:
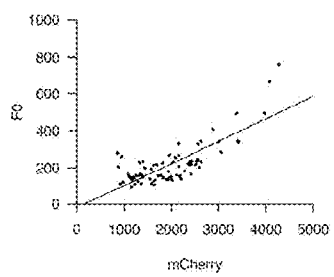
FIG. 6A shows the F0 relationship with mCherry fluorescence.
Figure 6B:
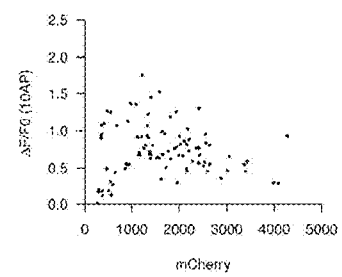
FIG. 6B shows the ΔF/F0 (10AP) response relationship with mCherry fluorescence.
Figure 6C:
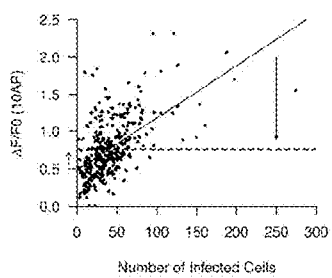
FIG. 6C shows the median ΔF/F0 (10AP) response dependency on the number of infected cells. Solid line: linear fit, slope=0.007.
Figure 6D:
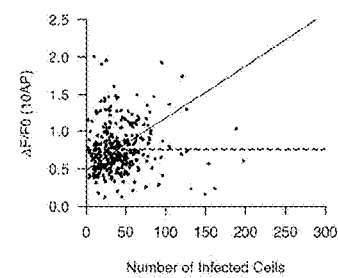
FIG. 6D is after compensation for density effect by subtraction of linear fit. Dashed line: linear fit, slope=0.

Nuclear mCherry fluorescence levels were correlated with GCaMP3 basal fluorescence (FIG. 6A, linear regression, $R^2=0.70$, $F(1,64)=154$, $p<2.2\times10^{-16}$). In screening, mCherry was thus used to normalize basal fluorescence values for GCaMP3 variants with variable F0 related to mutations. The ΔF/F0 response to 10AP was not strongly dependent on GCaMP expression levels as indicated by mCherry fluorescence (FIG. 6B). The GCaMP3 response of neurons was correlated with the number of infected neurons (FIG. 6C, linear regression, $R^2=0.32$, $F(1,320)=149.8$, $p<2.2\times10^{-16}$), possibly due to incomplete blockade of network function at higher densities. This relationship was used to correct for response variability. Without identifying underlying sources of variable responses, well-to-well differences were normalized by compensating based on density. A linear fit of the median GCaMP3 ΔF/F0 responses in wells as a function of number of infected cells was calculated for wells from all plates. Compensated GCaMP3 values were obtained after adjusting the fitted line slope to zero (FIG. 6D). Data for tested variants were then compensated following this model.

Figure 6E:
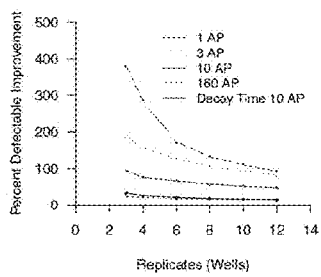
FIG. 6E is the percent detectable improvement relative to GCaMP3 performance estimated by simulating $10^5$ experiments using 3 to 12 replicate wells drawn from a data set of 322 replicate wells. The difference between the mean and the 99th percentile of simulated result distributions normalized by the mean defined the detection sensitivity at "=0.01 (red: 1AP, green: 3AP, blue: 10AP, magenta: 160AP, black: decay time (10AP)).

The detection sensitivity of the assay for improvements over GCaMP3 performance was estimated by examining the distribution of GCaMP3 responses across wells. Using uncompensated data from 322 GCaMP3 wells, random sets of 3, 4, 6, 8, 10, and 12 replicates $10^5$ times were selected to generate simulated distributions of GCaMP3 medians. The difference between the mean and the 99th percentile of these distributions normalized by the mean defined the detection sensitivity (for "=0.01). FIG. 6E shows the percent detectable improvement metrics of the assay as a function of replicates.

Figure 6F:
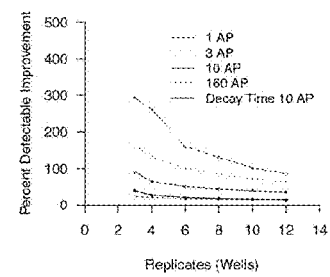
FIG. 6F is after compensation.

Increasing replicate number made the assay more sensitive. The assay was less sensitive with low AP stimulation. The same analysis was carried out using compensated data (FIG. 6F). Compensation improved sensitivity in the low AP range and with low replicates for ΔF/F0 measurements but not decay time measurements. With 8 replicates, 129%, 84%, 44%, and 16% ΔF/F0 improvements over GCaMP3 could be detected for 1, 3, 10, and 160AP stimulation, respectively (for "=0.01). With 8 replicates, 17% decay time improvements over GCaMP3 could be detected for 10AP stimulation (for "=0.01). Assay throughput was limited by the initial number of primary neurons prepared ($2.25\times10^5$ cells plated/well, mean of 41.3 ROI imaged/well) and the number of replicates tested for each GCaMP3 variant. For $22.5\times10^6$ cells (from ~12 neonatal rat pups) and 8 replicates per variant, 24 variants were tested in 16 h of imaging time, and ~240 GB of image data were generated.

Figure 7A:
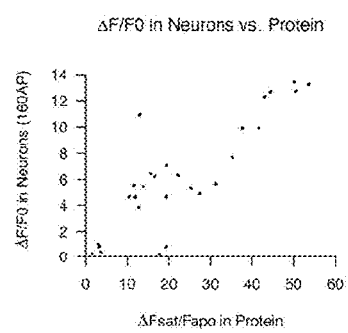
FIG. 7A shows the neuronal ΔF/F0 (160AP) of 28 GCaMP variants compared with mean protein $\Delta F_{sat}/F_{apo}$ (39 μM, highest concentration tested).
Figure 7B:
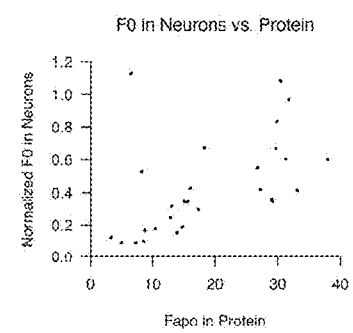
FIG. 7B shows the neuronal F0 (normalized by mCherry fluorescence) of variants compared with protein $F_{apo}$.
Figure 7C:
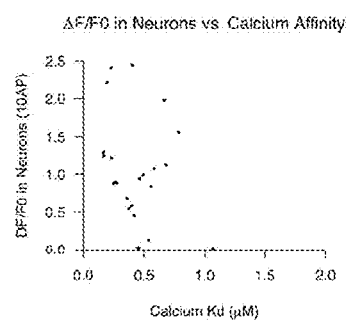
FIG. 7C shows the neuronal ΔF/F0 (10AP) of variants compared with protein calcium affinity ($K_d$).
Figure 7D:
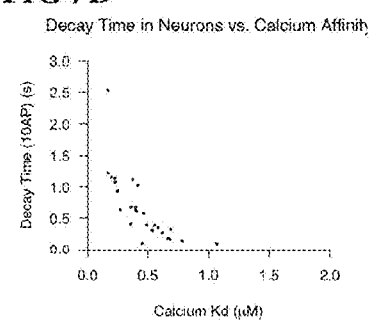
FIG. 7D shows the neuronal decay time (10AP) of variants compared with protein calcium affinity ($K_d$).
Figure 7E:
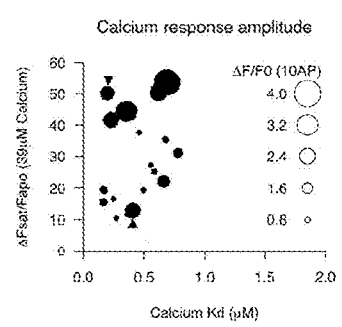
FIG. 7E shows the neuronal ΔF/F0 (10AP) of variants (diameter of circles) compared with protein $\Delta F_{sat}/F_{apo}$ and protein calcium affinity ($K_d$).
Figure 7F:
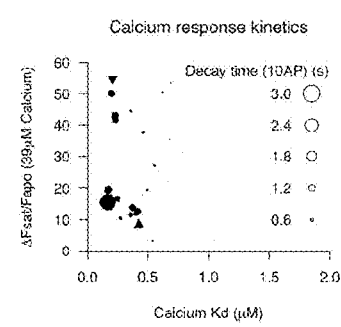
FIG. 7F shows the neuronal decay time (10AP) of variants (diameter of circles) compared with protein $\Delta F_{sat}/F_{apo}$ and protein calcium affinity ($K_d$).

Calcium titration experiments were carried out using purified protein and compared results with neuronal assay data for GCaMP3 and a sampling of screened variants made by site-directed mutagenesis. The uncompensated ΔF/F0 (160AP) response was correlated with the in vitro response to 39 μM calcium addition (FIG. 7A, linear regression, $R^2=0.71$, $F(1,26)=65.95$, $p=1.33\times10^{-8}$). The basal fluorescence in neurons was also correlated with apo state fluorescence of purified proteins (FIG. 7B, linear regression, $R^2=0.24$, $F(1,26)=9.685$, $p<0.01$). Purified protein assays were thus predictive for calcium response and basal fluorescence. Some variants with calcium affinities with $K_d<800$ nM were highly responsive to stimulus in neurons (FIG. 7C). But within this range, $K_d$ did not correlate with sensitivity in neurons. There was an inverse relationship between decay kinetics (10AP) in neurons and calcium affinity of proteins (FIG. 7D, nonlinear regression: decay time$=0.2302*K_d^{-0.8944}$, $R^2=0.72$, $F(1,26)=71.54$, $p=6.13\times10^{-9}$). Low calcium affinity was predictive for fast decay kinetics. But from $\Delta F_{sat}/F_{apo}$ and $K_d$ protein parameters alone, it was difficult to predict both neuronal ΔF/F0 and decay kinetics for a variant. For example, some variants exhibited 5-fold differences in $\Delta F_{sat}/F_{apo}$ in purified protein measurements, but they showed similar ΔF/F0 and decay kinetics in neurons and similar calcium affinities (FIG. 7E, 7F—arrows). The value of testing in neurons was thus that ΔF/F0 and decay kinetics could simultaneously be measured under realistic conditions where calcium dynamics in terms of speed and amplitude were in the relevant range for neurophysiology.

Example 10—Characterization of GCaMP6 Variants

Figure 8A:
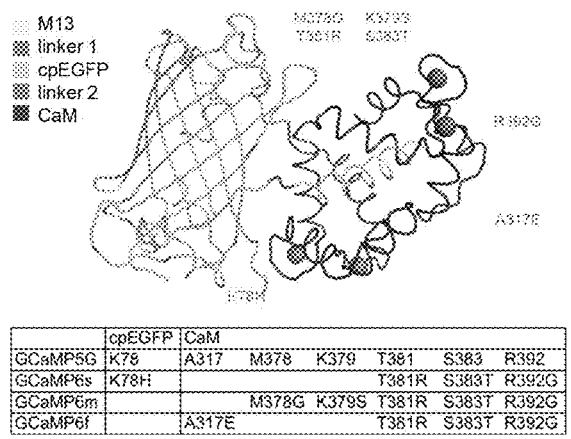
FIG. 8A shows the GCaMP2 protein structure (Akerboom et al., 2009, J. Biol. Chem., 284:6455-64) with locations of GCaMP6 mutations (red), M13 peptide (yellow), N-terminal linker (linker 1, gray), cpEGFP (green), C-terminal linker (linker 2, gray), and calcium ions (gray spheres). Mutations comparing GCaMP5G (Akerboom et al., 2012, J. Neurosci., 32:13819-40) and GCaMP6s ("slow"), GCaMP6m ("medium"), and GCaMP6f ("fast") are shown in the table ("FP"=field potential; 1 field stimulation evokes 1 action potential in the neurons).

More than 400 of the mutant GCaMP3 constructs were screened using this platform and three novel variants were identified with improved neuronal response properties compared with GCaMP3 and GCaMP5G (Akerboom et al., 2012, J. Neurosci., 32:13819-40). These novel variants were named GCaMP6s, GCaMP6m, and GCaMP6f, distinguished by their response kinetics (slow, medium, fast). FIG. 8A shows the amino acid sequence composition of GCaMP6s, GCaMP6m, and GCaMP6f relative to GCaMP5G. Four or five amino acids were changed relative to GCaMP5G.

In GCaMP6s, four changes were made that remodeled the proto-interface between the circularly permuted EGFP (cpEGFP), calmodulin (CaM), and N-terminal linker (linker 1) domains. These interface mutations included K78H in cpEGFP and T381R and S383T in CaM. Remodeling of the surfaces that affect the packing of the calcium bound form of the molecule could have beneficial effects on the bright state by occluding solvent access to the chromophore, which quenches fluorescence. Additionally, the R392G mutation in CaM has been shown to increase the calcium affinity, which would be predicted to increase the sensitivity of the indicator (VanScyoc et al., 2002, Biophys. J., 83:2767-80). In GCaMP6m, five changes were made relative to GCaMP5G. These included four interface mutations in CaM (M378G, K379S, T381R, S383T) and the R392G mutation. In GCaMP6f, four changes were made relative to GCaMP5G. These were two interface mutations in CaM (T381R, S383T), the R392G mutation, and the A317E mutation, which would be predicted to make the interaction between M13 and calcium-bound CaM less favorable. The A317E mutation causes the onset and offset of calcium-dependent fluorescence faster by destabilizing the M13/CaM interaction but lowers the ΔF/F0 response. This kinetic mutation was combined with the interface and affinity improvements to engineer an indicator with dual fast kinetics and enhanced calcium responsiveness.

The performance characteristics of GCaMP6s, GCaMP6m, and GCaMP6f on the screening platform are shown in FIG. 8B-8F. These novel variants were compared with GCaMP3, GCaMP5G, and the synthetic calcium indicator dye Oregon Green BAPTA-1 (ogb1).

Figure 8B:
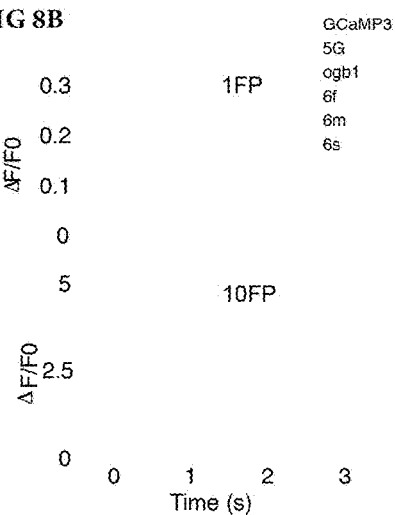
FIG. 8B shows the neuronal ΔF/F0 (1FP and 10FP) responses over time on the culture platform for GCaMP3 (red), GCaMP5G (green), Oregon Green BAPTA-1 (OGB-1) (blue), GCaMP6f (cyan), GCaMP6m (magenta), and GCaMP6s (black).
Figure 8C:
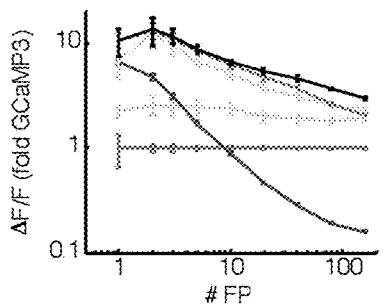
FIG. 8C shows the neuronal ΔF/F0 peak responses (median±sem).

In terms of peak ΔF/F0 response to 1FP stimulation, GCaMP6s, GCaMP6m, GCaMP6f, and ogb1 exhibited 6.8-, 6.7-, 4.9-, and 4.7-fold, respectively, greater responses than GCaMP5G (FIG. 8C). For 10FP stimulation, GCaMP6s, GCaMP6m, and GCaMP6f exhibited 4.5-, 4.2-, and 3.2-fold, respectively, greater responses than GCaMP5G.

Figure 8D:
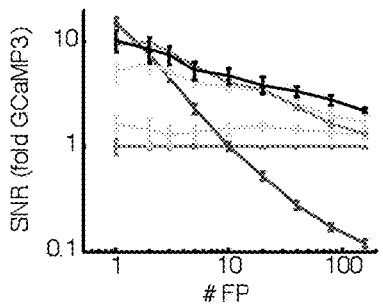
FIG. 8D shows the neuronal signal-to-noise ratios.

In terms of the signal-to-noise ratio (SNR) of the peak response to 1FP stimulation, ogb1, GCaMP6s, GCaMP6m, and GCaMP6f exhibited 9.7-, 8.0-, 7.5-, and 5.0-fold, respectively, greater SNR than GCaMP5G (FIG. 8D). For 10FP stimulation, GCaMP6s, GCaMP6m, and GCaMP6f exhibited 5.0-, 4.3-, and 4.0-fold, respectively, greater SNR than GCaMP5G.

Figure 8E:
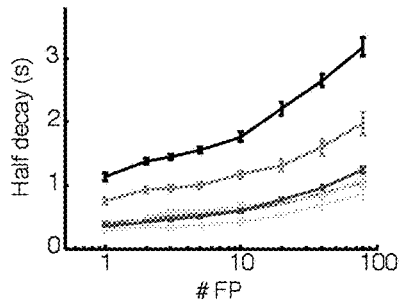
FIG. 8E shows the neuronal decay kinetics from peak fluorescence to half of peak.

In terms of the decay kinetics, the time for decay to half of peak fluorescence was compared. After 10FP stimulation, GCaMP6f was 24% faster than GCaMP5G (FIG. 8E). GCaMP6m and GCaMP6s were and 54% and 144% slower, respectively, than GCaMP5G.

Figure 8F:
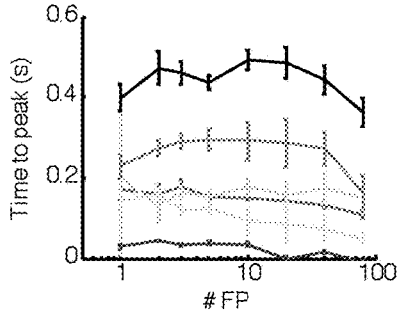
FIG. 8F shows the neuronal rise kinetics from stimulus onset to peak fluorescence.

In terms of the rise kinetics, the time to reach peak fluorescence was compared. After 10FP stimulation, GCaMP6f and ogb1 were 42% and 70% faster, respectively, than GCaMP5G (FIG. 8F). GCaMP6m and GCaMP6s were and 57% and 154% slower, respectively, than GCaMP5G.

In purified protein measurements, the calcium dissociation constants for GCaMP5G, GCaMP6s, GCaMP6m, and GCaMP6f were 422 nM, 157 nM, 162 nM, and 364 nM, respectively. The ΔFsat/Fapo for these indicators were 38.8, 61.2, 29.9, and 42.4, respectively. Unexpectedly, the ΔFsat/Fapo for GCaMP6m was below that for GCaMP5G and GCaMP6f, and yet it outperformed GCaMP5G and GCaMP6f in cultured neurons in terms of peak ΔF/F0 (FIG. 8B-8C). The higher affinity of GCaMP6m for calcium compared with GCaMP5G and GCaMP6f and the fact that neuronal free calcium concentrations are in the hundreds of nM range likely explain this difference. This underscores the superiority of screening GECIs in neurons compared with purified protein because calcium levels are in the relevant ranges.

The GCaMP6 variants exhibited ΔF/F0 responses to 1AP stimulation that were substantially augmented over GCaMP5G and GCaMP3 responses and were comparable with responses from the synthetic calcium indicator dye ogb1. Reaching the 1AP sensitivity level of this synthetic dye, which has been used to detect 1AP responses in rat cortical neurons in vivo with 97% accuracy (Kerr et al., 2005, PNAS USA, 102:14063-8), indicates that these variants will be capable of 1AP sensitivity in in vivo imaging experiments with similar accuracy. Additionally, GCaMP6f exhibited faster decay kinetics than GCaMP5G, which will enable better resolution of spiking from higher frequency firing neurons.

Example 11—Detection of Action Potentials In Vivo

Figure 9A:
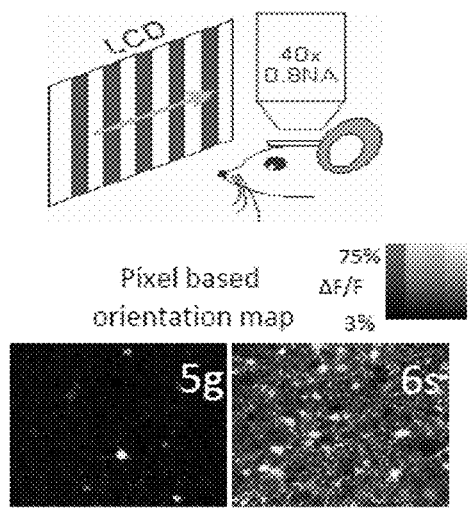
FIG. 9A-top shows the experimental setup to evaluate the performance of GCaMP3, GCaMP5G GCaMP5K (Akerboom et al., 2012, J. Neurosci., 32:13819-40), GCaMP6s, GCaMP6m, and GCaMP6f variants in an in vivo assay in mouse primary visual cortex (V1) pyramidal neurons. GCaMP variants were expressed in layer2/3 V1 pyramidal neurons by infection from an AAV2/1-hSynapsin1-GCaMP virus encoding one of the variants: the target neurons are imaged through a 2-photon microscope as visual stimuli are shown to the lightly anesthetized mouse.
Figure 9B:
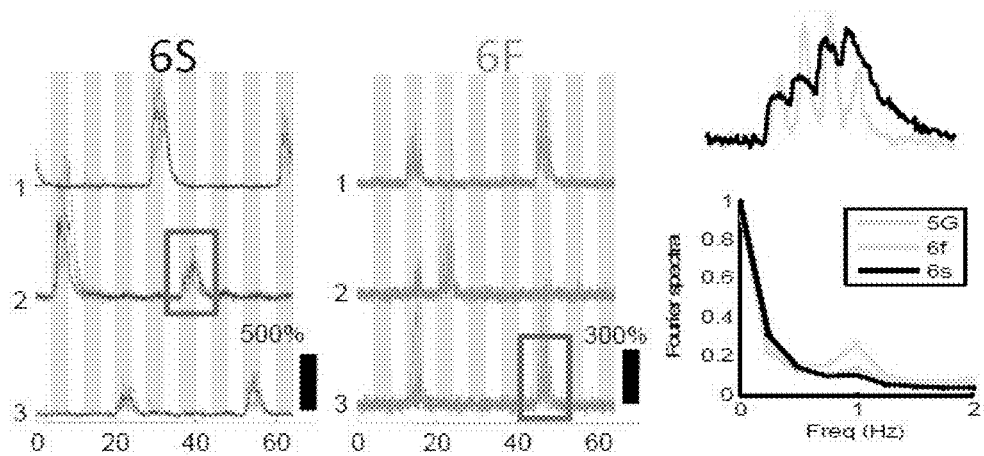
FIG. 9B shows representative fluorescent traces from neurons infected with either GCaMP6s ("6S") or GCaMP6f ("6F"), receiving identical visual stimuli. The boxes highlight traces of activity (shown overlaid in the graph in the top right of FIG. 9B), where the significantly faster rise and decay kinetics of GCaMP6f ("fast") relative to GCaMP6s ("slow") are easily seen. A Fourier spectrum overlay of responses from GCaMP5G GCaMP6s and GCaMP6f to identical stimuli is shown in the graph in the bottom right of FIG. 9B, showing the peak at 1 Hz, only discernible for GCaMP6f, corresponding to the 1 Hz frequency of the visual stimulus. Thus GCaMP6f more accurately determines the temporal structure of spike trains than previous sensors.
Figure 9C:
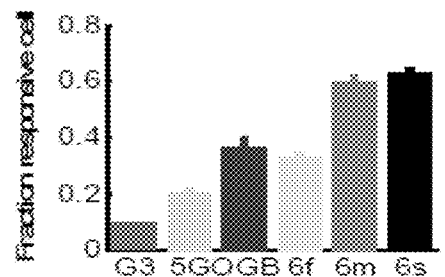
FIG. 9C shows the fraction of total pyramidal cells annotated as visually responsive for the five GCaMP indicators and for the dye, OGB-1. GCaMP6m and GCaMP6s annotate significantly more cells as visually responsive, more even than the state-of-the-art dye OGB-1.
Figure 9D:
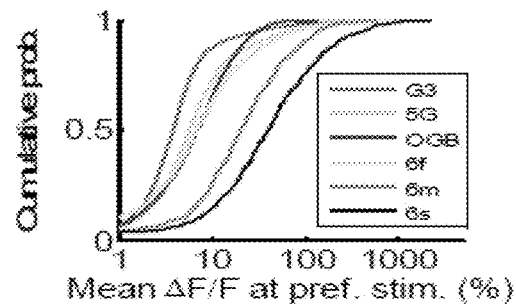
FIG. 9D shows the cumulative histogram of mean ΔF/F at the preferred visual stimulus orientation. The rightward shift of the GCaMP6s curve relative to the other calcium indicators shows its greater sensitivity.
Figure 9E:
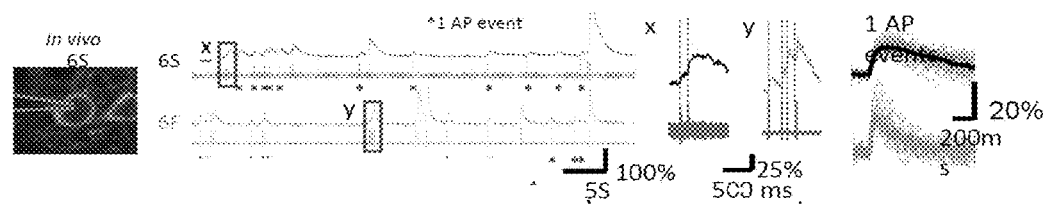
FIG. 9E shows a photo-graph of a fluorescence micrograph of a pyramidal neuron in vivo with a cell-attached recording electrode outlined and a simultaneous fluorescence imaging traces together with recorded spikes for GCaMP6s (top) and GCaMP6f (bottom). Both indicators detect single-action potential events. For multiple-AP events, GCaMP6f shows faster return-to-baseline than GCaMP6s, resulting in more easily deconvolved and quantitated spike trains; "x" and "y" show aligned fluorescence transients for the boxed 1-AP events, showing the faster rise & decay of GCaMP6f relative to GCaMP6s.
Figure 9F:
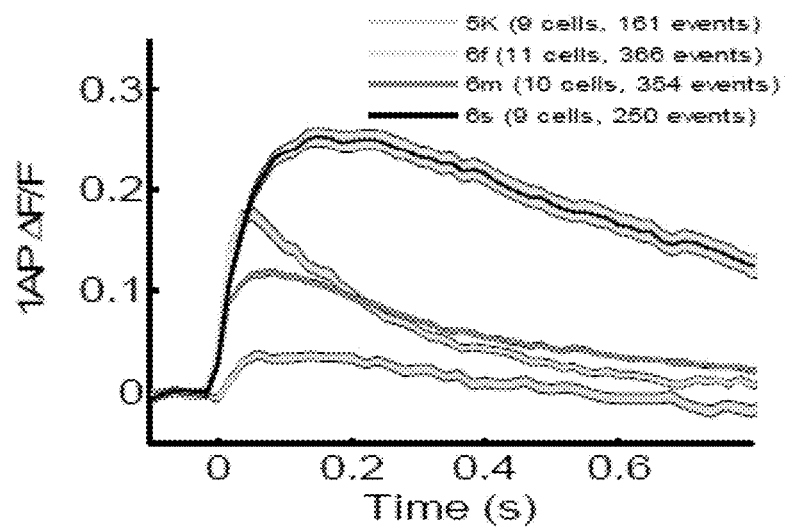
FIG. 9F shows aligned 1AP transients for the three GCaMP6 indicators and GCaMP5K.
Figure 9G:
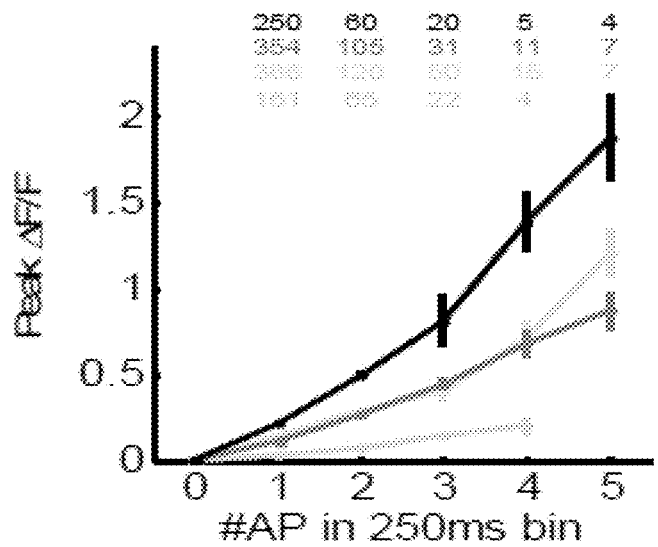
FIG. 9G shows responses of the four indicators to small spike trains of size 1-5 APs.
Figure 9H:
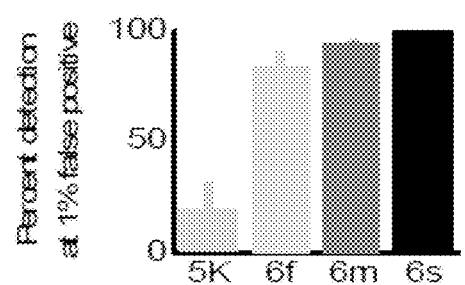
FIG. 9H shows the results of automated spike detection algorithms fitting the observed fluorescence traces to find spikes at a 1% false-positive rate. The three GCaMP6 indicators correctly find many more spikes at the same false-positive rate than GCaMP5K.
Figure 9I:
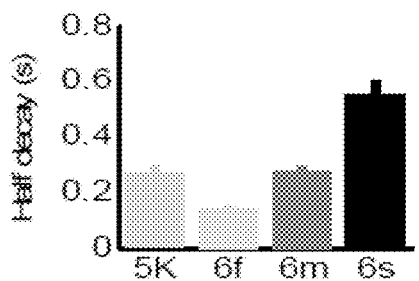
FIG. 9I shows the time-to-half-decay of the four indicators, following the peak of a 1 AP response. GCaMP6f is the fastest indicator, and GCaMP6s is the slowest.

GCaMP6s detected smaller bursts of APs in cultured neurons and, thus, was tested in vivo as well. GCaMP6s was expressed in V1 via transduction with AAV2/1-synapsin1-GCaMP6s virus, which labels pyramidal cells in layer2/3. Mice that had been labeled with GCaMP6s for 2 weeks were then lightly anesthetized and shown moving-grating visual stimuli, with a 2-photon microscope on their heads imaging activity (FIG. 9A-top). Moving gratings were shown in 8 directions, corresponding to 4 orientations of the compass. In parallel, separate mice were infected with GCaMP3, GCaMP5G, GCaMP6f or GCaMP6m virus and imaged identically. Separate mice were incubated with Oregon Green BAPTA-1 (OGB-1) and imaged identically. GCaMP6s annotated significantly more of a representative field of view to be visually responsive than GCaMP5G (FIG. 9B-bottom). Furthermore, GCaMP5G annotated only cell somata, whereas GCaMP6s annotated significant stretches of neuropil as visually responsive as well (FIG. 9A-bottom). For identical visual stimuli, GCaMP6s showed stronger fluorescence responses than GCaMP6f (FIG. 9B-left), but the rise and decay kinetics of the GCaMP6f signals were significantly faster than for GCaMP6s (FIG. 9B-right). GCaMP6s and GCaMP6m annotated ~60% of total labeled cells in V1 as being visually responsive, whereas GCaMP5G annotated ~20%, GCaMP3 annotated ~8%, and OGB-1 annotated ~40% (FIG. 9C). Thus, the GCaMP6s and GCaMP6m indicators are significantly more sensitive than previous GECIs and state-of-the-art calcium dyes. Cumulative distributions of the mean fluorescence increases at the preferred visual stimulus orientation corresponded to the fraction of visually responsive cells annotated, with the additional feature that GCaMP6s gave 2-3× the fluorescence increase as GCaMP6m (FIG. 9D). Cell-attached electrophysiological recordings performed simultaneously as 2-photon fluorescence imaging showed that action potentials corresponded exactly with fluorescence transients, and that single-AP events were robustly detected (FIG. 9E-left). Furthermore, with GCaMP6f 1-AP events produced fluorescence transients with significantly faster rise and decay kinetics than GCaMP6s (FIG. 9E-right). Spike trains of multiple APs were also more efficiently decoded with GCaMP6f than GCaMP6s (FIG. 9E-middle). Fluorescence responses of all three GCaMP6 indicators were substantially better than for GCaMP5K (FIG. 9F, 9G). GCaMP6s detected ~100% of recorded action potentials at a 1% false positive rate (FIG. 9H); GCaMP6m detected ~95%, GCaMP6f ~80%, and GCaMP5K ~20%. Time-to-half-decay from 1-AP events detected with GCaMP6f was ~100 milliseconds, for GCaMP6m ~200 ms, and for GCaMP6s ~500 ms (FIG. 9I). Taken together, these results show that the GCaMP6 indicators are significantly improved relative to the best state-of-the-art GECIs and calcium dyes in terms of detecting action potentials in vivo. GCaMP6f offers the additional advantage of showing dramatically improved temporal resolution, to better quantitate spike timing of individual APs, and to accurately deconvolve spike trains into their component APs.

Example 12—Detection of Single-Spine Activity In Vivo

In addition to better detecting action potentials that propagate through the entirety of neurons, more sensitive GECIs are also useful for detecting small calcium fluxes in specialized post-synaptic compartments, dendritic spine heads. These small calcium fluxes, in the absence of a global response of the cell, likely indicate $Ca^{2+}$ flux through glutamate receptors in the spine head, in response to glutamate molecules released from pre-synaptic cells in response to their firing APs. In this instance, such $Ca^{2+}$ transients are referred to as excitatory post-synaptic currents (EPSCs).

Figure 10A:
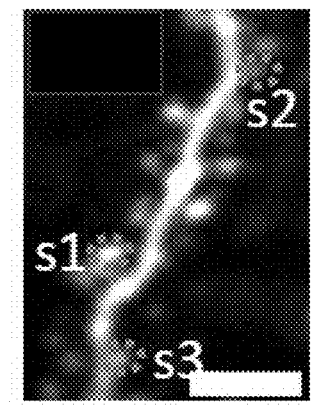
FIG. 10A shows baseline GCaMP6s fluorescence in a segment of L2/3 pyramidal cell dendrite, with three spines of interest labeled as s1, s2, and s3.
Figure 10B:
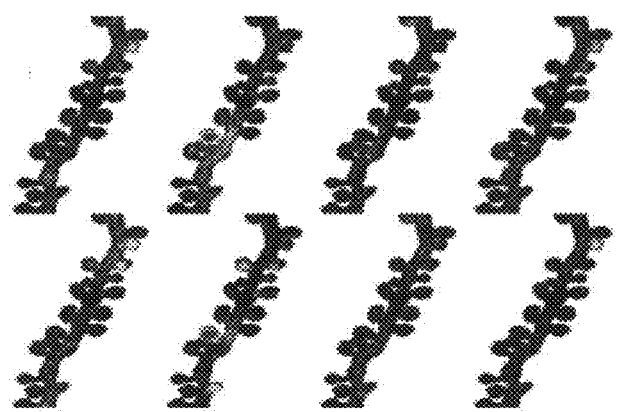
FIG. 10B shows maps of fluorescence change (dF=Fresponse−Fbaseline; heat map: blue=little change, red=large changes) in response to moving-grating visual stimuli in 8 different orientations.
Figure 10C:
FIG. 10C shows a color-coded map of orientation selectivity (4 primary orientations=red, cyan, green, yellow) overlaid on the mean fluorescence image.
Figure 10D:
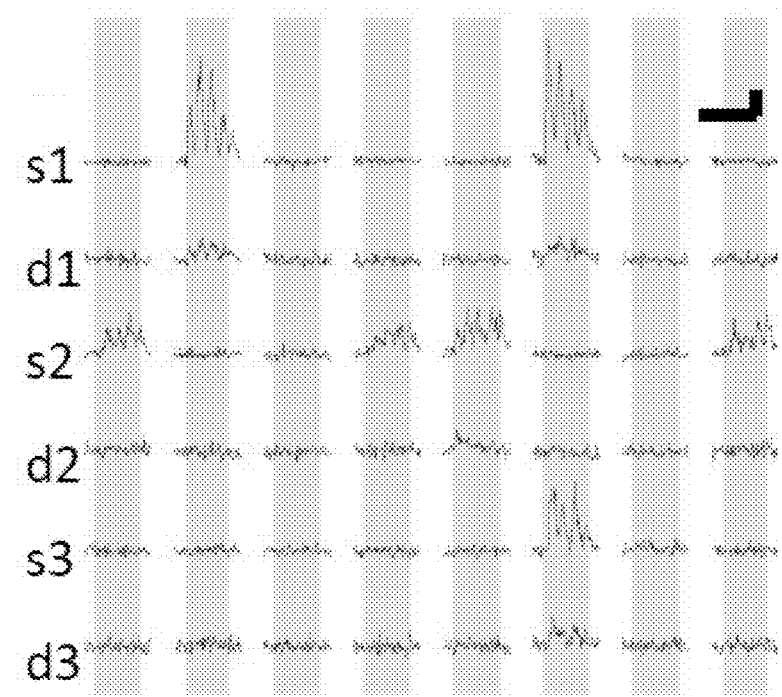
FIG. 10D shows fluorescence response traces of the regions marked in FIG. 10A, d1, d2, and d3 are the dendritic segments proximal to the three labeled spine heads. The three spine heads show significantly larger responses to moving-grating stimuli than the associated dendrite, and these responses are orientation-selective.
Figure 10E:
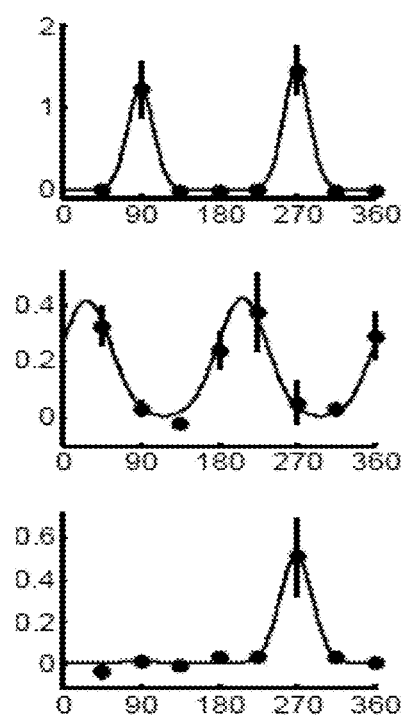
FIG. 10E shows the orientation tuning curves of the three spines shown in FIG. 10A. Spine s1 is sharply orientation-selective, spine s2 is gradually orientation-selective, and spine s3 is sharply direction-selective.
Figure 10F:
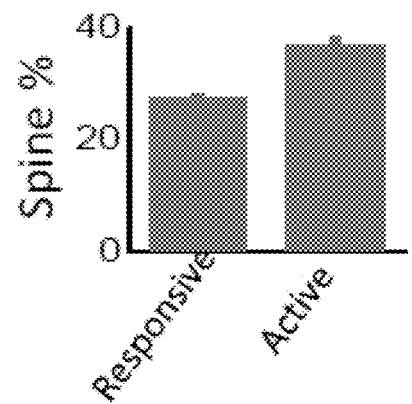
FIG. 10F shows the percentage of visually responsive and active spine (n=228 spines, 15 dendrites, 4 animals).
Figure 10G:
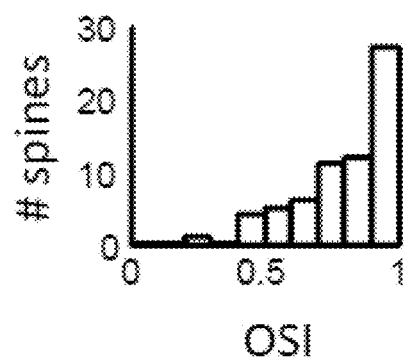
FIG. 10G shows the distribution of orientation selectivity index (OSI) of visually responsive spines (62 spines). Most of the visually responsive spines showed strong orientation selectivity.
Figure 10H:
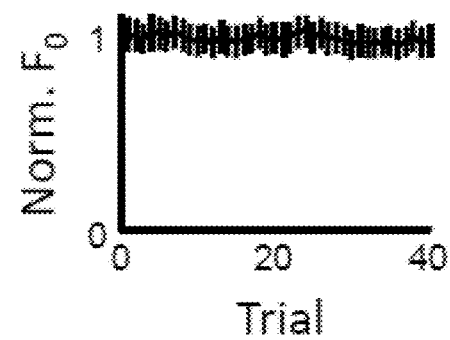
FIG. 10H shows the normalized baseline GCaMP6s fluorescence (Fo) over repeated imaging trials. The baseline fluorescence is remarkably stable, suggesting little photobleaching, gross synaptic plasticity affecting GCaMP6s expression levels, or dramatic changes in resting activity.
Figure 10I:
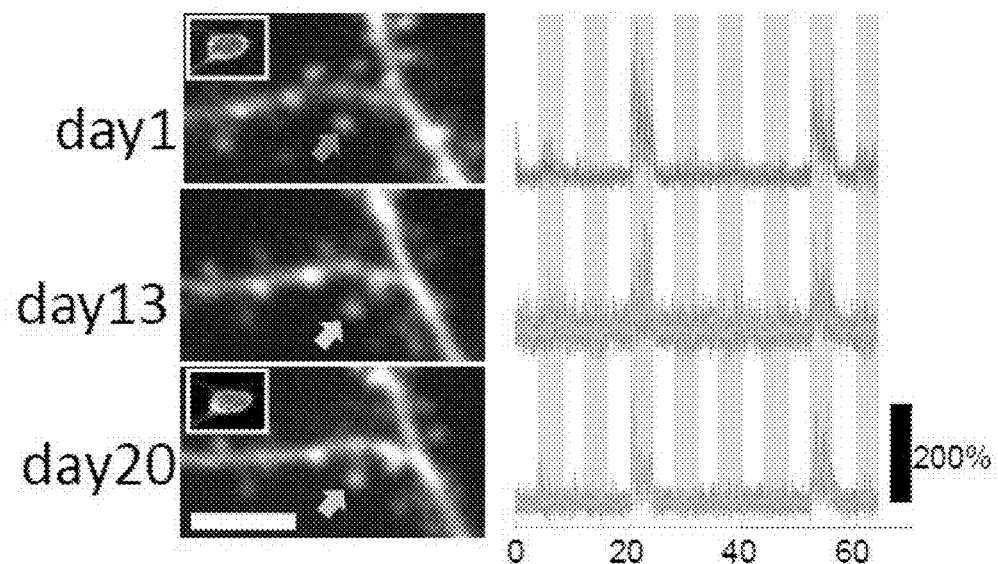
FIG. 10I-left shows fluorescence micrographs of a single GCaMP6s-labeled spine identified and repeatedly imaged daily up to three weeks. The insets show the cell body, indicating that there is no "cytomorbid" nuclear filling, which has been associated with GCaMP-induced cytotoxicity.
Figure 10J:
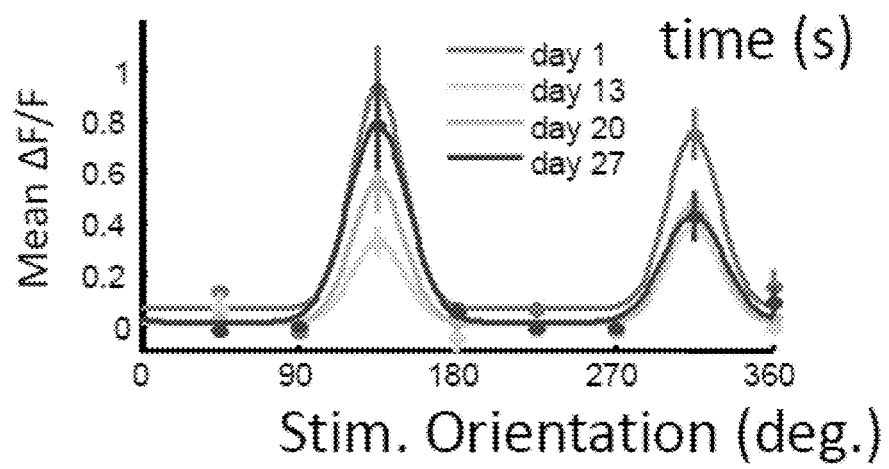
FIG. 10J shows the orientation-tuning curve of the same spine in FIG. 10I over days. The orientation selectivity of the spine is quite stable, although the magnitude of the single-spine response varies slightly over the imaging trials.
Figure 10K:
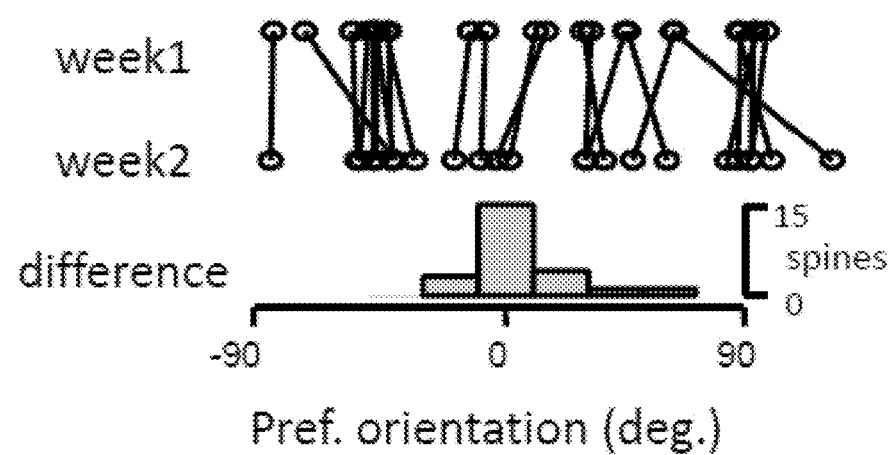
FIG. 10K-top shows the preferred orientation of the spines that responded in both imaging session (day0 and day7).

As in Example 9, GCaMP6s was expressed in V1 via transduction with AAV2/1-synapsin1-GCaMP6s virus, which labels pyramidal cells in layer2/3. Mice that had been labeled with GCaMP6s for 2 weeks were then lightly anesthetized and shown moving-grating visual stimuli, with a 2-photon microscope on their heads imaging activity. Visual stimuli were identical to those used in Example 9. Individual labeled spine heads along dendritic segments were clearly resolved with 2-photon imaging (FIG. 10A). In some cases, moving-grating visual stimuli evoked large, reproducible responses in single spines, in the absence of responses along the associated dendritic segment or the rest of the neuron (FIG. 10B). These robust single-spine responses also showed strong orientation selectivity (FIG. 10C), colored as in Example 9. Fluorescence transients from the single spines were large and showed faster kinetics than the action potential responses shown in Example 9 (FIG. 10D). Some spines showed sharp orientation selectivity (FIG. 10E-top), moderate orientation selectivity (FIG. 10E-middle), or sharp direction selectivity (FIG. 10E-bottom). ~40% of spines were active during the visual stimuli, and ~25% of spines were orientation- or direction-selective (FIG. 10F). Most active spines showed some orientation selectivity (FIG. 10G). The baseline fluorescence of single spines, imaged daily over 3 weeks, was quite stable (FIG. 10H). This indicates that there is little photobleaching over the trials, and that little gross synaptic plasticity occurs to increase or decrease GCaMP6s expression levels. Baseline spine activity also seems to be similar over the three weeks. Responses of the single spines to moving grating stimuli were also quite stable over three weeks (FIG. 10I-right); furthermore, labeled cells did not show "cytomorbid" nuclear filling (FIG. 10I-left-insets), which has been associated with GCaMP-induced cytotoxicity. Orientation selectivity of most imaged spines remained stable over three weeks: an example spine is shown in FIG. 10J. Over all imaged spines, most did not shift their orientation selectivity between week 1 and week 2; those that did shifted it by up to 75 degrees (FIG. 10K). Taken together, these results show that the new GCaMP6 indicators disclosed herein facilitate long-term in vivo single-spine imaging, an application that has not been feasible with previous GECIs and dyes. This enables a new set of experiments to deconvolve the activity of individual spines and dendrites during behavior, and the contribution of synaptic activity to the function of neurons and neural circuits.

Example 13—Orientation Domains in GABAergic Dendrites

How orientation-tuned neurons connect to other orientation-tuned neurons remains controversial. Some measurements suggest that individual neurons sample inputs essentially randomly and models indicate that specific connectivity is not required for orientation tuning. Other measurements find that neurons prefer to make synapses with neurons sharing similar orientation tuning, but orientation tuning at the level of subthreshold membrane potential is weak. To address this issue, neurons with tuned output (OSI, 0.91±0.04, n=5) were identified (FIG. 11A) and the orientation tuning of large numbers of dendritic spines was measured per neuron (average, 201; range, 120-298) (FIG. 11B-11D). Contributions to the signal from back-propagating action potentials were removed using a computational subtraction procedure (Methods; FIG. 14). For individual neurons, the orientation tuning averaged across all spines was biased towards the orientation tuning of the parent neurons (FIG. 11E, 11F) ($p<0.01$), although the modulation depth was smaller ($p<0.01$). A similar trend was also apparent in the distributions of preferred orientations across spines (FIG. 11G, 11H). These results show that average synaptic NMDA-R currents, an important components of excitatory synaptic input, share orientation tuning with the cell's output.

GCaMP6s also reported activity in GABAergic neurons, which produce relatively small action potential-dependent calcium accumulations (FIGS. 12A and 15). Consistent with previous results, somatic fluorescence changes in GABAergic neurons were untuned with respect to stimulus orientation (FIG. 12B). However, their dendrites showed pronounced orientation-tuned domains (FIG. 12C, 12D). Individual dendritic branches often had multiple domains with distinct preferred orientations. The underlying fluorescence responses were modulated at the temporal frequency of the drifting grating (1 Hz) (FIG. 12E), a characteristic feature of V1 excitatory neurons, suggesting that the responses reflect excitatory synaptic input. Tuned dendritic domains were seen in parvalbumin-positive (FIG. 12A) and somatostatin-positive interneurons.

Figure 13A:
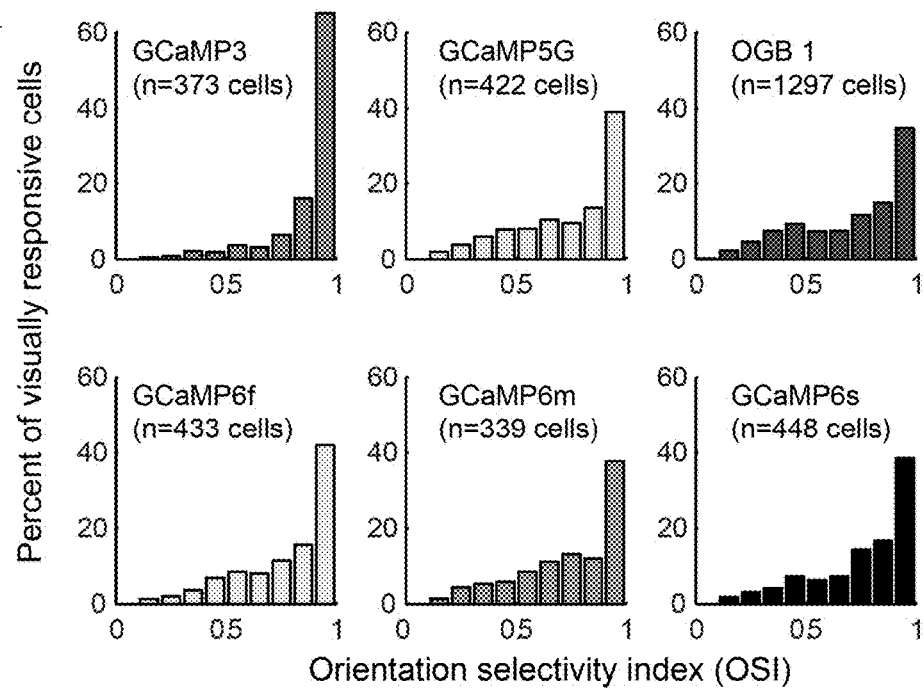
FIG. 13A shows the distribution of orientation selectivity index (OSI) of visually responsive cells measured using different sensors.
Figure 13B:
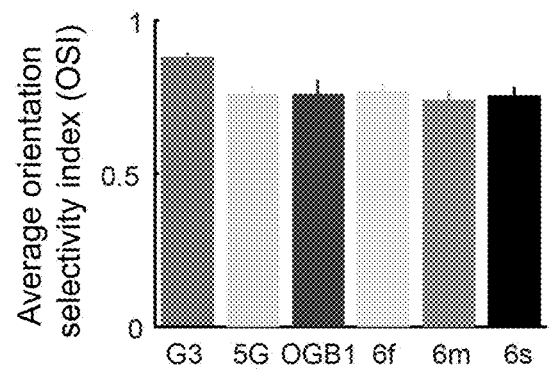
FIG. 13B shows the average OSI across sensors.
Figure 15A:
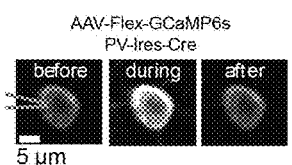
FIG. 15A shows an image of a PV neuron labeled with GCaMP6s before (left), during (middle) and after (right) visual stimulation (as in FIG. 9).
Figure 15C:
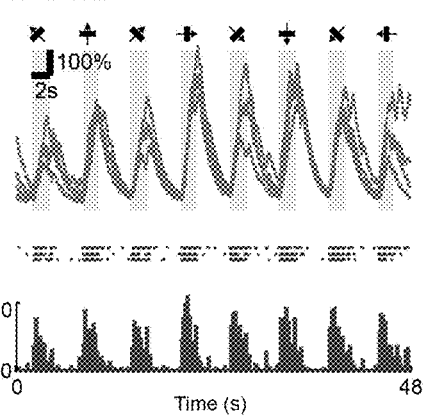
FIG. 15C shows the fluorescence response of a GCaMP6s labeled PV cell (top, gray: individual trial; red, average of 3 trials) and corresponding spike raster (middle) and peristimulus time histogram (bottom) during the presentation of eight drifting grating stimuli.
Figure 15D:
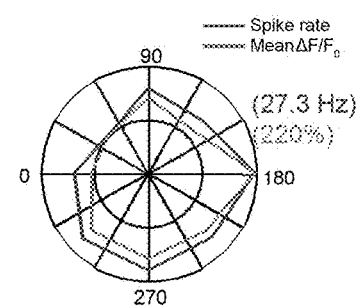
FIG. 15D shows the mean fluorescence response (red) and spike rate (blue) of the neuron in FIG. 15C in response to gratings with different orientations.
Figure 15B:
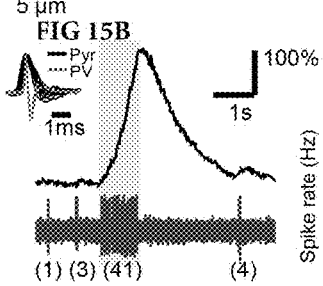
FIG. 15B shows the fluorescence signal (top) and simultaneously recorded spikes (bottom) of a PV cell in response to visual stimulation. The number of spikes in each burst is indicated below the spike trace. Inset, averaged spike waveform of recorded PV cells (red) compared to pyramidal cells (black, recorded in wild-type mice).
Figure 15E:
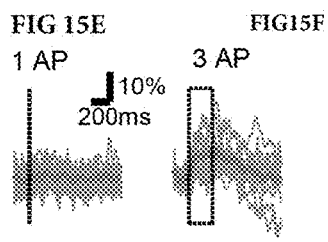
FIG. 15E shows the fluorescence change in response to one (left) and three (right) APs. Gray: single trials; Red: average of all trials.
Figure 15F:
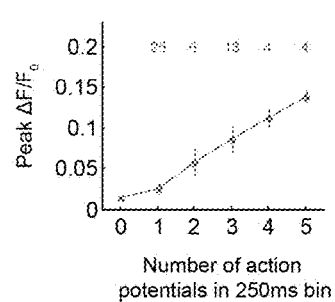
FIG. 15F shows the fluorescence change as a function of number of APs in a 250 ms bin.
Figure 15G:
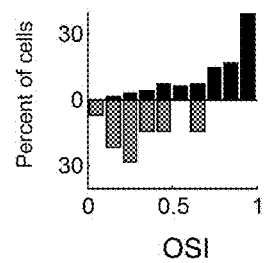
FIG. 15G shows the distribution of orientation selectivity index (OSI) of PV cells (red) and pyramidal cells (black).
Figure 16A:
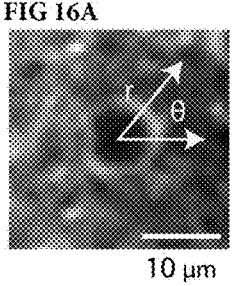
FIG. 16A shows a GCaMP-labeled cell. The user starts the ROI selection process by clicking at the cell center. The algorithm first calculates the intensity profile in a polar coordinate around the click location (FIG. 16B), and determines a closed path (curves in FIGS. A, B and C) that maximizes the summed intensity along the path.
Figure 16B:
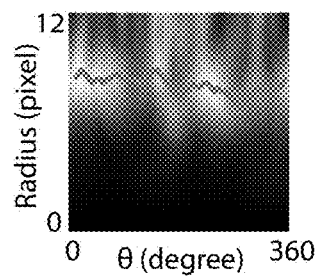
FIG. 16D shows an example region of interest output by the algorithm.
FIG. 16E shows an example field of view with many GCaMP labeled cells.
FIG. 16F shows regions of interests covering GCaMP labeled cells in the field of view.
Figure 16C:
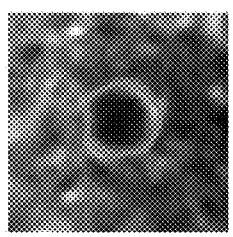
Figure 16D:
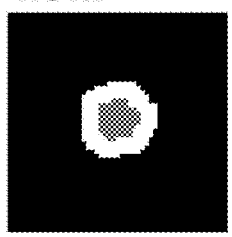
Figure 16E:
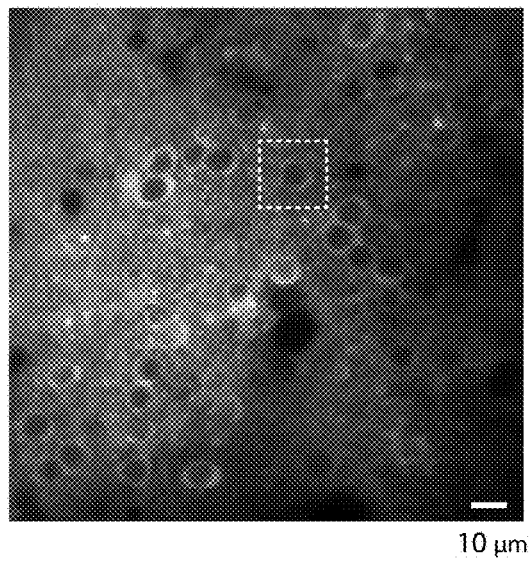
Figure 16F:
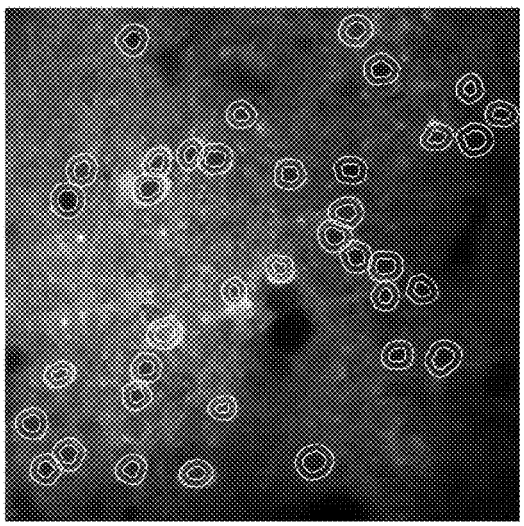

The visual response was mapped along 104 interneuron dendrites (total imaged length 6.3 mm). Regions of interests were placed every micrometer of dendritic length (FIG. 12D). Visually-evoked GCaMp6s responses were detected in 5.7 mm (90%) of dendritic length, with 1.79 mm (28%) showing significant orientation-tuning ($p<0.01$, ANOVA across 8 conditions). The majority of imaged dendrites (33/54; longer than 50 μm) had multiple domains preferring different orientations. The OSI (0.44±0.15; mean±SD) of the dendritic domains was higher than for interneuron somata ($p<0.005$, FIG. 15), but lower than for typical pyramidal neurons ($p<0.001$, FIG. 13). Back-propagation of untuned somatic action potentials likely lowers the OSI of the dendritic calcium signals. Consistent with this, both the dendritic OSI and the percentage of orientation selective sites increased with distance from soma (FIG. 12F).

The sizes of individual domains (12.5±7 μm FWHM mean±SD) were considerably larger than the spacing between excitatory synapses on interneuron dendrites (<1 μm) (FIG. 12G). In many cases, spatial overlap was observed between nearby domains with distinct preferred orientations (FIG. 12H). These domains might reflect spatially clustered input with shared orientation preference. Postsynaptic mechanisms of amplification might also contribute.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A nucleic acid molecule encoding a genetically encoded calcium indicator (GECI) polypeptide, wherein the GECI polypeptide comprises an amino acid sequence having at least 99% sequence identity to the sequence as set forth in SEQ ID NO: 10.

2. The nucleic acid molecule of claim 1, wherein the GECI comprises SEQ ID NO:10.

3. The nucleic acid molecule of claim 1, wherein the nucleic acid molecule comprises the sequence as set forth in SEQ ID NO:9.

4. A vector comprising the nucleic acid molecule of claim 1.

5. An isolated cell comprising the vector of claim 4.

6. An isolated cell comprising the nucleic acid molecule of claim 1.

7. A GECI polypeptide, wherein the polypeptide comprises an amino acid sequence having at least 99% sequence identity to the sequence shown in SEQ ID NO:10.

8. The polypeptide of claim 7, wherein the polypeptide comprises the amino acid sequence shown in SEQ ID NO:10.

9. A cell comprising a polypeptide of claim 7.

* * * * *

SEQUENCE LISTING

<160> NUMBER OF SEQ ID NOS: 10

<210> SEQ ID NO 1
<211> LENGTH: 1350
<212> TYPE: DNA
<213> ORGANISM: Artificial Sequence
<220> FEATURE:
<223> OTHER INFORMATION: oligonucleotide

<400> SEQUENCE: 1

```
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca acgagaagcg cgatcacatg gtcctgctgg agttcgtgac cgccgccggg     420
atcactctcg gcatggacga gctgtacaag ggcggtaccg agggagcat ggtgagcaag      480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca gacccgcgc cgaggtgaag ttcgagggcg acaccctggt gaaccgcatc      840
gagctgaagg gcatcgactt caaggaggac ggcaacatcc tggggcacaa gctggagtac     900
aacctgccgg accaactgac tgaagagcag atcgcagaat taaagaggc tttctcccta      960 tttgacaagg acggggatgg gacaataaca accaaggagc tgggacggt gatgcggtct     1020 ctggggcaga accccacaga agcagagctg caggacatga tcaatgaagt agatgccgac    1080
ggtgacggca caatcgactt ccctgagttc ctgacaatga tggcaagaaa aatgaaatac    1140
acagacagtg aagaagaaat tagagaagcg ttccgtgtgt ttgataagga tgcaatggc     1200 tacatcagtg cagcagagct tcgccacgtg atgacaaacc ttgagagaa gttaacagat    1260 gaagaggttg atgaaatgat cagggaagca gacatcgatg gggatggtca ggtaaactac    1320
```

```
gaagagtttg tacaaatgat gacagcgaag                                        1350
```

<210> SEQ ID NO 2
<211> LENGTH: 450
<212> TYPE: PRT
<213> ORGANISM: Artificial Sequence
<220> FEATURE:
<223> OTHER INFORMATION: synthetic peptide

<400> SEQUENCE: 2

```
Met Gly Ser His His His His His His Gly Met Ala Ser Met Thr Gly
  1               5                  10                  15

Gly Gln Gln Met Gly Arg Asp Leu Tyr Asp Asp Asp Lys Asp Leu
             20                  25                  30

Ala Thr Met Val Asp Ser Ser Arg Arg Lys Trp Asn Lys Thr Gly His
             35                  40                  45

Ala Val Arg Ala Ile Gly Arg Leu Ser Ser Leu Glu Asn Val Tyr Ile
         50                  55                  60

Lys Ala Asp Lys Gln Lys Asn Gly Ile Lys Ala Asn Phe Lys Ile Arg
 65                  70                  75                  80

His Asn Ile Glu Asp Gly Gly Val Gln Leu Ala Tyr His Tyr Gln Gln
                 85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
        130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350
```

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
        370                 375                 380

Glu Glu Ile Arg Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr
        435                 440                 445

Ala Lys
    450

<210> SEQ ID NO 3
<211> LENGTH: 1350
<212> TYPE: DNA
<213> ORGANISM: Artificial Sequence
<220> FEATURE:
<223> OTHER INFORMATION: oligonucleotide

<400> SEQUENCE: 3
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt caagatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360 aaagaccccca acgagaagcg cgatcacatg gtcctgctgg agttcgtgac cgccgccggg     420
atcactctcg gcatggacga gctgtacaag ggcggtaccg agggagcat ggtgagcaag     480 ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacacgcgtg accaactgac tgaagagcag atcgcagaat ttaaagaggc tttctcccta     960
tttgacaagg acggggatgg gacaataaca accaaggagc tggggacggt gatgcggtct    1020
ctggggcaga accccacaga agcagagctg caggacatga tcaatgaagt agatgccgac    1080
ggtgacggca aatcgactt ccctgagttc ctgacaatga tggcaagaaa aatgaaatac    1140
acagacagtg aagaagaaat tgagaagcg ttccgtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                    1350

<210> SEQ ID NO 4

```
<211> LENGTH: 450
<212> TYPE: PRT
<213> ORGANISM: Artificial Sequence
<220> FEATURE:
<223> OTHER INFORMATION: synthetic peptide

<400> SEQUENCE: 4

Met Gly Ser His His His His His His Gly Met Ala Ser Met Thr Gly
1               5                   10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
            35                  40                  45

Ala Val Arg Ala Ile Gly Arg Leu Ser Ser Leu Glu Asn Val Tyr Ile
50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
            115                 120                 125

His Met Val Leu Leu Glu Phe Val Thr Ala Ala Gly Ile Thr Leu Gly
            130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
            195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
            275                 280                 285

Glu Asp Gly Asn Ile Leu Gly His Lys Leu Glu Tyr Asn Thr Arg Asp
            290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
            355                 360                 365

Glu Phe Leu Thr Met Met Ala Arg Lys Met Lys Tyr Thr Asp Ser Glu
            370                 375                 380
```

Glu Ile Gly Glu Ala Phe Arg Val Phe Asp Lys Asp Gly Asn Gly
385                 390                 395                 400

Tyr Ile Ser Ala Ala Glu Leu Arg His Val Met Thr Asn Leu Gly Glu
            405                 410                 415

Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
    435                 440                 445

Ala Lys
    450

<210> SEQ ID NO 5
<211> LENGTH: 1350
<212> TYPE: DNA
<213> ORGANISM: Artificial Sequence
<220> FEATURE:
<223> OTHER INFORMATION: oligonucleotide

<400> SEQUENCE: 5

```
atgggttctc atcatcatca tcatcatggt atggctagca tgactggtgg acagcaaatg      60
ggtcgggatc tgtacgacga tgacgataag gatctcgcca ccatggtcga ctcatcacgt     120
cgtaagtgga ataagacagg tcacgcagtc agagctatag gtcggctgag ctcactcgag     180
aacgtctata tcaaggccga caagcagaag aacggcatca aggcgaactt ccacatccgc     240
cacaacatcg aggacggcgg cgtgcagctc gcctaccact accagcagaa cacccccatc     300
ggcgacggcc ccgtgctgct gcccgacaac cactacctga gcgtgcagtc caaactttcg     360
aaagacccca cgagaagcg cgatcacatg gtcctgctgg agttcgtgac cgccgccggg     420
atcactctcg gcatggacga gctgtacaag gcggtaccg agggagcat ggtgagcaag       480
ggcgaggagc tgttcaccgg ggtggtgccc atcctggtcg agctggacgg cgacgtaaac     540
ggccacaagt tcagcgtgtc cggcgagggt gagggcgatg ccacctacgg caagctgacc     600
ctgaagttca tctgcaccac cggcaagctg cccgtgccct ggcccaccct cgtgaccacc     660
ctgacctacg gcgtgcagtg cttcagccgc taccccgacc acatgaagca gcacgacttc     720
ttcaagtccg ccatgcccga aggctacatc caggagcgca ccatcttctt caaggacgac     780
ggcaactaca agacccgcgc cgaggtgaag ttcgagggcg acaccctggt gaaccgcatc     840
gagctgaagg gcatcgactt caaggaggac ggcaacatcc tggggcacaa gctggagtac     900
aacctgccgg accaactgac tgaagagcag atcgcagaat ttaaagaggc tttctcccta     960
tttgacaagg acggggatgg acaataaca accaaggagc tggggacggt gatgcggtct    1020
ctggggcaga accccacaga agcagagctg caggacatga tcaatgaagt agatgccgac    1080
ggtgacggca caatcgactt ccctgagttc ctgacaatga tggcaagaaa aatgaaatac    1140
agggacacgg aagaagaaat tagagaagcg ttcggtgtgt ttgataagga tggcaatggc    1200
tacatcagtg cagcagagct tcgccacgtg atgacaaacc ttggagagaa gttaacagat    1260
gaagaggttg atgaaatgat cagggaagca gacatcgatg gggatggtca ggtaaactac    1320
gaagagtttg tacaaatgat gacagcgaag                                    1350
```

<210> SEQ ID NO 6
<211> LENGTH: 450
<212> TYPE: PRT
<213> ORGANISM: Artificial Sequence
<220> FEATURE:
<223> OTHER INFORMATION: synthetic peptide

<400> SEQUENCE: 6

| | | | | | | | | | | | | | | |
|---|---|---|---|---|---|---|---|---|---|---|---|---|---|---|
|Met|Gly|Ser|His|His|His|His|His|Gly|Met|Ala|Ser|Met|Thr|Gly|
|1| | | |5| | | | |10| | | | |15|

Gly Gln Gln Met Gly Arg Asp Leu Tyr Asp Asp Asp Lys Asp Leu
               20                  25                  30

Ala Thr Met Val Asp Ser Ser Arg Lys Trp Asn Lys Thr Gly His
         35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe His Ile Arg
65                  70                  75                  80

His Asn Ile Glu Asp Gly Gly Val Gln Leu Ala Tyr His Tyr Gln Gln
             85                  90                  95

Asn Thr Pro Ile Gly Asp Gly Pro Val Leu Leu Pro Asp Asn His Tyr
             100                 105                 110

Leu Ser Val Gln Ser Lys Leu Ser Lys Asp Pro Asn Glu Lys Arg Asp
             115                 120                 125

His Met Val Leu Leu Glu Phe Val Thr Ala Ala Gly Ile Thr Leu Gly
130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                 165                 170                 175

Gly Asp Val Asn Gly His Lys Phe Ser Val Ser Gly Glu Gly Glu Gly
             180                 185                 190

Asp Ala Thr Tyr Gly Lys Leu Thr Leu Lys Phe Ile Cys Thr Thr Gly
             195                 200                 205

Lys Leu Pro Val Pro Trp Pro Thr Leu Val Thr Thr Leu Thr Tyr Gly
210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                 245                 250                 255

Phe Lys Asp Asp Gly Asn Tyr Lys Thr Arg Ala Glu Val Lys Phe Glu
             260                 265                 270

Gly Asp Thr Leu Val Asn Arg Ile Glu Leu Lys Gly Ile Asp Phe Lys
             275                 280                 285

Glu Asp Gly Asn Ile Leu Gly His Lys Leu Glu Tyr Asn Leu Pro Asp
290                 295                 300

Gln Leu Thr Glu Glu Gln Ile Ala Glu Phe Lys Glu Ala Phe Ser Leu
305                 310                 315                 320

Phe Asp Lys Asp Gly Asp Gly Thr Ile Thr Thr Lys Glu Leu Gly Thr
                 325                 330                 335

Val Met Arg Ser Leu Gly Gln Asn Pro Thr Glu Ala Glu Leu Gln Asp
             340                 345                 350

Met Ile Asn Glu Val Asp Ala Asp Gly Asp Gly Thr Ile Asp Phe Pro
355                 360                 365

Glu Phe Leu Thr Met Met Ala Arg Lys Met Lys Tyr Arg Asp Thr Glu
                 370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu

```
            405                 410                 415
Lys Leu Thr Asp Glu Glu Val Asp Glu Met Ile Arg Glu Ala Asp Ile
        420                 425                 430

Asp Gly Asp Gly Gln Val Asn Tyr Glu Glu Phe Val Gln Met Met Thr
        435                 440                 445

Ala Lys
    450
```

```
<210> SEQ ID NO 7
<211> LENGTH: 1350
<212> TYPE: DNA
<213> ORGANISM: Artificial Sequence
<220> FEATURE:
<223> OTHER INFORMATION: oligonucleotide

<400> SEQUENCE: 7
```

| | | | | | |
|---|---|---|---|---|---|
| atgggttctc | atcatcatca | tcatcatggt | atggctagca | tgactggtgg | acagcaaatg | 60 |
| ggtcgggatc | tgtacgacga | tgacgataag | gatctcgcca | ccatggtcga | ctcatcacgt | 120 |
| cgtaagtgga | ataagacagg | tcacgcagtc | agagctatag | gtcggctgag | ctcactcgag | 180 |
| aacgtctata | tcaaggccga | caagcagaag | aacggcatca | aggcgaactt | caagatccgc | 240 |
| cacaacatcg | aggacggcgg | cgtgcagctc | gcctaccact | accagcagaa | cacccccatc | 300 |
| ggcgacggcc | ccgtgctgct | gcccgacaac | cactacctga | gcgtgcagtc | caaactttcg | 360 |
| aaagacccca | acgagaagcg | cgatcacatg | gtcctgctgg | agttcgtgac | cgccgccggg | 420 |
| atcactctcg | gcatggacga | gctgtacaag | ggcggtaccg | agggagcat | ggtgagcaag | 480 |
| ggcgaggagc | tgttcaccgg | ggtggtgccc | atcctggtcg | agctggacgg | cgacgtaaac | 540 |
| ggccacaagt | tcagcgtgtc | cggcgagggt | gagggcgatg | ccacctacgg | caagctgacc | 600 |
| ctgaagttca | tctgcaccac | cggcaagctg | cccgtgccct | ggcccaccct | cgtgaccacc | 660 |
| ctgacctacg | gcgtgcagtg | cttcagccgc | taccccgacc | acatgaagca | gcacgacttc | 720 |
| ttcaagtccg | ccatgcccga | aggctacatc | caggagcgca | ccatcttctt | caaggacgac | 780 |
| ggcaactaca | agacccgcgc | cgaggtgaag | ttcgagggcg | acaccctggt | gaaccgcatc | 840 |
| gagctgaagg | gcatcgactt | caaggaggac | ggcaacatcc | tggggcacaa | gctggagtac | 900 |
| aacctgccgg | accaactgac | tgaagagcag | atcgcagaat | ttaaagagga | attctcccta | 960 |
| tttgacaagg | acggggatgg | gacaataaca | accaaggagc | tggggacggt | gatgcggtct | 1020 |
| ctggggcaga | accccacaga | agcagagctg | caggacatga | tcaatgaagt | agatgccgac | 1080 |
| ggtgacggca | caatcgactt | ccctgagttc | ctgacaatga | tggcaagaaa | aatgaaatac | 1140 |
| agggacacgg | aagaagaaat | tagagaagcg | ttcggtgtgt | ttgataagga | tggcaatggc | 1200 |
| tacatcagtg | cagcagagct | tcgccacgtg | atgacaaacc | ttggagagaa | gttaacagat | 1260 |
| gaagaggttg | atgaaatgat | cagggaagca | gacatcgatg | gggatggtca | ggtaaactac | 1320 |
| gaagagtttg | tacaaatgat | gacagcgaag | | | | 1350 |

```
<210> SEQ ID NO 8
<211> LENGTH: 450
<212> TYPE: PRT
<213> ORGANISM: Artificial Sequence
<220> FEATURE:
<223> OTHER INFORMATION: synthetic peptide

<400> SEQUENCE: 8
```

```
Met Gly Ser His His His His His His Gly Met Ala Ser Met Thr Gly
1               5                   10                  15
```

```
Gly Gln Gln Met Gly Arg Asp Leu Tyr Asp Asp Asp Lys Asp Leu
             20                  25                  30

Ala Thr Met Val Asp Ser Ser Arg Lys Trp Asn Lys Thr Gly His
         35                  40                  45

Ala Val Arg Ala Ile Gly Arg Leu Ser Ser Leu Glu Asn Val Tyr Ile
 50                  55                  60

Lys Ala Asp Lys Gln Lys Asn Gly Ile Lys Ala Asn Phe Lys Ile Arg
 65                  70                  75                  80

His Asn Ile Glu Asp Gly Gly Val Gln Leu Ala Tyr His Tyr Gln Gln
             85                  90                  95

Asn Thr Pro Ile Gly Asp Gly Pro Val Leu Leu Pro Asp Asn His Tyr
             100                 105                 110

Leu Ser Val Gln Ser Lys Leu Ser Lys Asp Pro Asn Glu Lys Arg Asp
         115                 120                 125

His Met Val Leu Leu Glu Phe Val Thr Ala Ala Gly Ile Thr Leu Gly
 130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
             165                 170                 175

Gly Asp Val Asn Gly His Lys Phe Ser Val Ser Gly Glu Gly Glu Gly
             180                 185                 190

Asp Ala Thr Tyr Gly Lys Leu Thr Leu Lys Phe Ile Cys Thr Thr Gly
         195                 200                 205

Lys Leu Pro Val Pro Trp Pro Thr Leu Val Thr Thr Leu Thr Tyr Gly
         210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                 245                 250                 255

Phe Lys Asp Asp Gly Asn Tyr Lys Thr Arg Ala Glu Val Lys Phe Glu
             260                 265                 270

Gly Asp Thr Leu Val Asn Arg Ile Glu Leu Lys Gly Ile Asp Phe Lys
         275                 280                 285

Glu Asp Gly Asn Ile Leu Gly His Lys Leu Glu Tyr Asn Leu Pro Asp
 290                 295                 300

Gln Leu Thr Glu Glu Gln Ile Ala Glu Phe Lys Glu Phe Ser Leu
305                 310                 315                 320

Phe Asp Lys Asp Gly Asp Gly Thr Ile Thr Thr Lys Glu Leu Gly Thr
             325                 330                 335

Val Met Arg Ser Leu Gly Gln Asn Pro Thr Glu Ala Glu Leu Gln Asp
         340                 345                 350

Met Ile Asn Glu Val Asp Ala Asp Gly Asp Gly Thr Ile Asp Phe Pro
         355                 360                 365

Glu Phe Leu Thr Met Met Ala Arg Lys Met Lys Tyr Arg Asp Thr Glu
         370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                 405                 410                 415

Lys Leu Thr Asp Glu Glu Val Asp Glu Met Ile Arg Glu Ala Asp Ile
         420                 425                 430
```

Asp Gly Asp Gly Gln Val Asn Tyr Glu Glu Phe Val Gln Met Met Thr
        435                 440                 445

Ala Lys
    450

<210> SEQ ID NO 9
<211> LENGTH: 1350
<212> TYPE: DNA
<213> ORGANISM: Artificial Sequence
<220> FEATURE:
<223> OTHER INFORMATION: oligonucleotide

<400> SEQUENCE: 9

| | |
|---|---|
| atgggttctc atcatcatca tcatcatggt atggctagca tgactggtgg acagcaaatg | 60 |
| ggtcgggatc tgtacgacga tgacgataag gatctcgcca ccatggtcga ctcatcacgt | 120 |
| cgtaagtgga ataagacagg tcacgcagtc agagctatag gtcggctgag ctcactcgag | 180 |
| aacgtctata tcaaggccga caagcagaag aacggcatca aggcgaactt caagatccgc | 240 |
| cacaacatcg aggacggcgg cgtgcagctc gcctaccact accagcagaa cacccccatc | 300 |
| ggcgacggcc ccgtgctgct gcccgacaac cactacctga gcgtgcagtc caaactttcg | 360 |
| aaagacccca cgagaagcg cgatcacatg gtcctgctgg agttcgtgac cgccgccggg | 420 |
| atcactctcg gcatggacga gctgtacaag ggcggtaccg agggagcat ggtgagcaag | 480 |
| ggcgaggagc tgttcaccgg ggtggtgccc atcctggtcg agctggacgg cgacgtaaac | 540 |
| ggccacaagt tcagcgtgtc cggcgagggt gagggcgatg ccacctacgg caagctgacc | 600 |
| ctgaagttca tctgcaccac cggcaagctg cccgtgccct ggcccaccct cgtgaccacc | 660 |
| ctgacctacg gcgtgcagtg cttcagccgc taccccgacc acatgaagca gcacgacttc | 720 |
| ttcaagtccg ccatgcccga aggctacatc caggagcgca ccatcttctt caaggacgac | 780 |
| ggcaactaca agacccgcgc cgaggtgaag ttcgagggcg acaccctggt gaaccgcatc | 840 |
| gagctgaagg gcatcgactt caaggaggac ggcaacatcc tggggcacaa gctggagtac | 900 |
| aacctgccgg accaactgac tgaagagcag atcgcagaat ttaaagagga attctcccta | 960 |
| tttgacaagg acggggatgg gacaataaca accaaggagc tggggacggt gatgcggtct | 1020 |
| ctggggcaga accccacaga agcagagctg caggacatga tcaatgaagt agatgccgac | 1080 |
| ggtgacggca aatcgactt ccctgagttc ctgacaatga tggcaagaaa aatgaaatac | 1140 |
| agggacacgg aagaagaaat tagagaagcg ttcggtgtgt ttgataagga tggcaatggc | 1200 |
| tacatcagtg cagcagagct tcgccacgtg atgacaaacc ttggagagaa gttaacagat | 1260 |
| gaagaggttg atgaaatgat cagggaagca gacatcgatg gggatggtca ggtaaactac | 1320 |
| gaagagtttg tacaaatgat gacagcgaag | 1350 |

<210> SEQ ID NO 10
<211> LENGTH: 450
<212> TYPE: PRT
<213> ORGANISM: Artificial Sequence
<220> FEATURE:
<223> OTHER INFORMATION: synthetic peptide

<400> SEQUENCE: 10

Met Gly Ser His His His His His His Gly Met Ala Ser Met Thr Gly
  1               5                  10                  15

Gly Gln Gln Met Gly Arg Asp Leu Tyr Asp Asp Asp Lys Asp Leu
            20                  25                  30

Ala Thr Met Val Asp Ser Ser Arg Arg Lys Trp Asn Lys Thr Gly His
        35                  40                  45

Ala Val Arg Ala Ile Gly Arg Leu Ser Ser Leu Glu Asn Val Tyr Ile
    50                  55                  60

Lys Ala Asp Lys Gln Lys Asn Gly Ile Lys Ala Asn Phe Lys Ile Arg
65                  70                  75                  80

His Asn Ile Glu Asp Gly Gly Val Gln Leu Ala Tyr His Tyr Gln Gln
                85                  90                  95

Asn Thr Pro Ile Gly Asp Gly Pro Val Leu Leu Pro Asp Asn His Tyr
            100                 105                 110

Leu Ser Val Gln Ser Lys Leu Ser Lys Asp Pro Asn Glu Lys Arg Asp
        115                 120                 125

His Met Val Leu Leu Glu Phe Val Thr Ala Ala Gly Ile Thr Leu Gly
    130                 135                 140

Met Asp Glu Leu Tyr Lys Gly Gly Thr Gly Gly Ser Met Val Ser Lys
145                 150                 155                 160

Gly Glu Glu Leu Phe Thr Gly Val Val Pro Ile Leu Val Glu Leu Asp
                165                 170                 175

Gly Asp Val Asn Gly His Lys Phe Ser Val Ser Gly Glu Gly Glu Gly
            180                 185                 190

Asp Ala Thr Tyr Gly Lys Leu Thr Leu Lys Phe Ile Cys Thr Thr Gly
        195                 200                 205

Lys Leu Pro Val Pro Trp Pro Thr Leu Val Thr Thr Leu Thr Tyr Gly
    210                 215                 220

Val Gln Cys Phe Ser Arg Tyr Pro Asp His Met Lys Gln His Asp Phe
225                 230                 235                 240

Phe Lys Ser Ala Met Pro Glu Gly Tyr Ile Gln Glu Arg Thr Ile Phe
                245                 250                 255

Phe Lys Asp Asp Gly Asn Tyr Lys Thr Arg Ala Glu Val Lys Phe Glu
            260                 265                 270

Gly Asp Thr Leu Val Asn Arg Ile Glu Leu Lys Gly Ile Asp Phe Lys
        275                 280                 285

Glu Asp Gly Asn Ile Leu Gly His Lys Leu Glu Tyr Asn Leu Pro Asp
    290                 295                 300

Gln Leu Thr Glu Glu Gln Ile Ala Glu Phe Lys Glu Phe Ser Leu
305                 310                 315                 320

Phe Asp Lys Asp Gly Asp Gly Thr Ile Thr Thr Lys Glu Leu Gly Thr
                325                 330                 335

Val Met Arg Ser Leu Gly Gln Asn Pro Thr Glu Ala Glu Leu Gln Asp
            340                 345                 350

Met Ile Asn Glu Val Asp Ala Asp Gly Asp Gly Thr Ile Asp Phe Pro
        355                 360                 365

Glu Phe Leu Thr Met Met Ala Arg Lys Met Lys Tyr Arg Asp Thr Glu
    370                 375                 380

Glu Glu Ile Arg Glu Ala Phe Gly Val Phe Asp Lys Asp Gly Asn Gly
385                 390                 395                 400

Tyr Ile Ser Ala Ala Glu Leu Arg His Val Met Thr Asn Leu Gly Glu
                405                 410                 415

Lys Leu Thr Asp Glu Glu Val Asp Glu Met Ile Arg Glu Ala Asp Ile
            420                 425                 430

Asp Gly Asp Gly Gln Val Asn Tyr Glu Glu Phe Val Gln Met Met Thr

```
               435                 440                 445
Ala Lys
    450
```